(12) United States Patent
Neuman

(10) Patent No.: US 8,753,607 B2
(45) Date of Patent: Jun. 17, 2014

(54) METHODS AND KITS FOR THE DIFFERENTIAL DIAGNOSIS OF ALZHEIMER'S DISEASE VERSUS FRONTOTEMPORAL DEMENTIA AND FOR THE DIAGNOSIS OF FRONTOTEMPORAL DEMENTIA, COMPRISING FAS-L AND CK 18 AS BIOMARKERS

(76) Inventor: Manuela G. Neuman, Toronto (CA)

(\*) Notice: Subject to any disclaimer, the term of this patent is extended or adjusted under 35 U.S.C. 154(b) by 0 days.

(21) Appl. No.: 13/185,831

(22) Filed: Jul. 19, 2011

(65) Prior Publication Data
US 2012/0015381 A1    Jan. 19, 2012

Related U.S. Application Data

(63) Continuation of application No. 12/922,775, filed as application No. PCT/CA2009/000346 on Mar. 20, 2009, now abandoned.

(60) Provisional application No. 61/038,475, filed on Mar. 21, 2008.

(51) Int. Cl.
*A61K 38/19* (2006.01)
*C07K 14/52* (2006.01)
*C07K 14/525* (2006.01)
*G01N 33/53* (2006.01)

(52) U.S. Cl.
USPC .............. 424/9.1; 702/19; 530/351; 530/361; 530/380; D24/107; D24/223

(58) Field of Classification Search
None
See application file for complete search history.

(56) References Cited

U.S. PATENT DOCUMENTS

| | | |
|---|---|---|
| 2004/0072261 A1 | 4/2004 | Kostanjevecki et al. |
| 2006/0094064 A1 | 5/2006 | Ray et al. |
| 2007/0037200 A1 | 2/2007 | Ray et al. |
| 2007/0042429 A1 | 2/2007 | Goldknopf et al. |
| 2007/0042437 A1 | 2/2007 | Wands et al. |
| 2007/0099203 A1 | 5/2007 | Zhang |
| 2007/0134726 A1 | 6/2007 | Hochstrasser et al. |
| 2007/0141023 A1 | 6/2007 | Ashkenazi et al. |

FOREIGN PATENT DOCUMENTS

| | | |
|---|---|---|
| WO | 2004001421 | 12/2003 |
| WO | 2004019043 | 3/2004 |
| WO | 2005047484 | 5/2005 |
| WO | 2005052592 | 6/2005 |
| WO | 2006003414 | 1/2006 |
| WO | 2006028586 | 3/2006 |
| WO | 2006113289 | 10/2006 |
| WO | 2006133423 | 12/2006 |
| WO | 2007136674 | 11/2007 |

OTHER PUBLICATIONS

Alvarez et al., Neurobiology of Aging, 28:533-536, published online Mar. 29, 2006.*
RayBio Human Fas Ligand ELISA kit protocol, 2004.*
Peviva M30 Apoptosense ELISA product information sheet, 2004.*
Choi et al., Brain Research Reviews, 44:65-81, 2004.*
Abraham, C. R., et al., "Immunochemical Identification of the Serine Protease Inhibitor α1-Antichymotrypsin in the Brain Amyloid Deposits of Alzheimer's Disease", Cell, vol. 52, 487-501 (1988).
Akiyama, H., et al., "Inflammation and Alzheimer's disease", Neurobiology of Aging 21(3), 383-421 (2000).
Baskin, F., et al., "Platelet APP isoform ratios correlate with declining cognition in AD", Neurology, 54, 1907-1909 (2000). (Abstract Only).
Becher, B., et al., "CD95-CD95L: can the brain learn from the immune system?" Trends in Neurosciences, vol. 21, No. 3, p. 114-116 (1998).
Benveniste, E.N., et al., "Differential regulation of astrocyte TNF-alpha expression by the cytokines TGF-beta, IL-6 and IL-10", Int. J. Devl Neuroscience, vol. 13, No. 3/4, 341-349 (1995).
Binetti, G, et al., "Differences between Pick disease and Alzheimer disease in clinical appearance and rate of cognitive decline", Arch Neurol, vol. 57: 225-232 (2000).
Bird, T.D., et al., "Frontotemporal dementia: genotypes, phenotypes and more problems to be solved", Neurobiology of Aging, 22:113-114 (2001).
Blasko, I,, et al., "TNFα plus INFÁ induce the production of Alzheimer β-amyloid peptides and decrease the secretion of APPs", FASEB J, vol. 13: 63-68 (1999).
Broe, M., et al., "Astrocytic degeneration relates to the severity of disease in frontotemporal dementia", Brain, vol. 127, No. 10, p. 2214-2220 (2004).
Chao, C.C., et al., "Transforming growth factor-beta is in Alzheimer's disease", Clinical and Diagnostic Laboratory Immunology, vol. 1: 109-110 (1994).
Colciaghi, F., et al., "Platelet APP, ADAM 10 and BACE alterations in the early stages of Alzheimer disease", Neurology, 62, 498-501 (2004).
Del Bo, R., et al., "Reciprocal control of inflammatory cytokines, IL-1 and IL-6, and beta- amyloid production in cultures", Neuroscience Letters, 188:70-74 (1995).
De Luigi, A., et al., "Inflammatory markers in Alzheimer's disease and multi-infarct dementia", Mechanisms of Ageing and Development, 122:1985-1995 (2001).
Diamandis, E. P., et al. "Human Kallikrein 6 as a Biomarker of Alzheimer's Disease", Clinical Biochemistry, vol. 33: 663-667 (2000).
Dobson, C. M., "Protein folding and misfolding", Nature, vol. 426: 884-890 (2003).

(Continued)

*Primary Examiner* — Daniel E Kolker
*Assistant Examiner* — Stacey N MacFarlane
(74) *Attorney, Agent, or Firm* — Dann, Dorfman, Herrell & Skillman; Kathleen D. Rigaut

(57) ABSTRACT

The invention relates to methods and kits for the differential diagnosis of Alzheimer's disease (AD) versus frontotemporal dementia (FTD), using biomarkers TNF-α, FAS-L and CK18, taken from a biological sample. Differences in biomarker levels can be used to distinguish between AD and FTD The invention is based on a discovered correlation between FTD and markers FAS-L and CK18. Therefore the invention also relates to the diagnosis of FTD using FAS-L and CK18. The serum concentrations of these biomarkers can further be used as an index of the severity of disease, and may occur in conjunction with clinical-based diagnostic testing and neuroimaging assessment.

6 Claims, 15 Drawing Sheets

(56) References Cited

OTHER PUBLICATIONS

Dong, Y, et al., "IFN-gamma regulation of the type IV class II transactivator promoter in astrocytes", J Immunol., 162 (8): 4731-4739 (1999).

Du, Y. et al., "Reduced levels of amyloid β-peptide antibody in Alzheimer disease", Neurology, 57,801-805 (2001).

Dziedzic, T. et al., "Dexamethasone Inhibits TNF-alpha Synthesis More Effectively in Alzheimer's Disease Patients than in Healthy Individuals", Dement Geriatr Cogn Disord, 16: 283-286 (2003).

Extended European Search Report corresponding to EP 2279420 dated Sep. 13, 2011.

Ferrer, I. et al., "Fas and Fas ligand expression in Alzheimer's disease". Acta neuropathologica, vol. 102, No. 2, p. 121-31 (2001).

Forman, M. S., et al., "Neurodegenerative diseases: a decade of discoveries paves the way for therapeutic breakthroughs", Nature Medicine, vol. 10,1055-1063 (2004).

Frohman, E.M., et al., "Expression of intercellullar adhesion molecule 1 (ICAM-1) in Alzheimer's disease". Journal of the Neurological Sciences, 106:105-111 (1991).

Gabbita, S. P., et al., "Increased Nuclear DNA Oxidation in the Brain in Alzheimer's Disease", Journal of Neurochemistry, 71, 2034-2040 (1998).

Gorlovoy, P. et al., "Accumulation of tau induced in neurites by microglial proinflammatory mediators", The FASEB Journal, vol. 23, pp. 2502-2513 (2009).

Guerreiro, R.J. et al., "Peripheral inflammatory cytokines as biomarkers in Alzheimer's disease and mild cognitive impairment", Neurodegenerative Disease 4(6):406-412 (2007). (Abstract Only).

Hampel, H. et al., "Discriminant power of combined cerebrospinal fluid τ protein and of the soluble interleukin-6 receptor complex in the diagnosis of Alzheimer's disease", Brain Research, 823, 104-112 (1999).

Hartmann, T., "Cholesterol, Aβ and Alzheimer's disease", Trends Neurosci. 24 (Suppl. 11), S45-S48 (2001).

Henriksson, T. et al., "Analysis and Quantitation of the β-Amyloid Precursor Protein in the Cerebrospinal Fluid of Alzheimer's Disease Patients with a Monoclonal Antibody-Based Innunoassay", J. Neurochem. 56, 1037-1042 (1991).

Hensley, K. et al., "Electrochemical Analysis of Protein Nitrotyrosine and Dityrosine in the Alzheimer Brain Indicates Region-Specific Accumulation", J. Neurosci. 18, 8126-8132 (1998).

Hodges, J.R., et al., "The differentiation of semantic dementia and frontal lobe dementia (temporal and frontal variants of frontotemporal dementia) from early Alzheimer's disease: A comparative neuropsychological study", Neuropsychology, 13(1):31-40, (1999).

Hof, P.R., et al., "Evidence for early vulnerability of the medial and inferior aspects of the temporal lobe in an 82-year-old patient with preclinical signs of dementia. Regional and laminar distribution of neurofibrillary tangles and senile plaques", Arch Neurol, 49:946-953 (1992).

Huberman, M., et al., "Correlation of cytokine secretion by mononuclear cells of Alzheimer patients and their disease stage", Elsevier Journal of Neuroimmunology, 52:147-152 (1994).

Hüll, M., et al., "Inflammatory mechanisms in Alzheimer's disease". Eur Arch Psychiatry Clin Neurosci. 246(3):124-8 (1996) (Abstract Only).

International Search Report published with International Publication No. WO 2009/114945 on Jul. 15, 2009.

Kennard, M. L., et al., "Serum levels of the iron binding protein p97 are elvated in Alzheimer's disease", Nature Medicine vol. 2, 1230-1235 (1996).

Kim, D. K. et al., "Serum Melanotransferrin, p97 as a Biochemical Marker of Alzheimer's Disease", Neuropsychopharmacology 25, 84-90 (2001).

Lanzrein, A. S. et al., "Longitudinal Study of Inflammatory Factors in Serum, Cerebrospinal Fluid, and Brain Tissue in Alzheimer Disease: Interleukin-1beta, Interleukin-6, Interleukin-1 Receptor Antagonist, Tumor Necrosis Factor-alpha, the Soluble Tumor Necrosis Factor Receptors I and II, and alpha1-Antichymotrypsin", Alzheimer Dis. Assoc. Disord. vol. 12, No. 3, pp. 215-227 (1998).

Laytragoon-Lewin, N, "Programmed cell death: the influence of CD40, CD95 (Fas or Apo-I) and their ligands". Medical Oncology, 15(1):15-19 (1998).

Licastro, F. et al., "Increased plasma levels of interleukin-1, interleukin-6 and alpha1-antichymotrypsin in patients with Alzheimer's disease: peripheral imflammation or signals from the brain?", J. Neuroimmunol. 103, 97-107 (2000).

Licastro, F. et al., "Increased serum alpha1-antichymotrypsin in patients with probable Alzheimer's disease: an acute phase reactant without the peripheral acute phase response", J. Neuroimmunol. 57, 71-75 (1995).

Liscic, R.M. et al., "Clinical and Psychometric Distinction of Frontotemporal and Alzheimer Dementias". Arch Neuro/vol. 64, 535-540 (2007).

Lombardi, V.R.M., et al., "Characterization of cytokine production, screening of lymphocyte subset patterns and in vitro apoptosis in healthy and Alzheimer's disease (AD) individuals", J Neuroimmunology 97:163-171 (1999).

Lou, Jau-Shin. "Amyotrophic lateral sclerosis". Clinical Summary, MedLink Neurology [online], [retrieved on Jun. 9, 2009]. Retrieved from the Internet: <URL: http://www.medlink.com/medlinkcontent.asp>.

Lovell, M. A. "Ratio of 8-Hydroxyguanine in Intact DNA to Free 8-Hydroxyguanane Is Increased in Alzheimer Disease Ventricular Cerebrospinal Fluid", Arch. Neurol. 58, 392-396 (2001).

Mathuranath, P.S., et al., "A brief cognitive test battery to differentiate Alzheimer's disease and frontotemporal dementia", Neurology 2000; 55:1613-1620.

Mattis, S., "Mental Status Examination for Organic Mental Syndrome in the Elderly Patient", In: Bellak L, Karasu TB, editors, Geriatric Psychiatry, New York: Grune and Stratton, 77-121 (1976).

McKhann, G, et al., "Clinical diagnosis of Alzheimer's disease: Report of the NINCDS-ADRDA work group under the auspices of Department of Health and Human Services Task Force on Alzheimer's disease". Neurology 34(7): 939-944 (1984). (Abstract Only).

Meda, L, et al., "Proinflammatory profile of cytokine production by human monocytes and murine microglia stimulated with β-amyloid[25-35]". J Neuroimmunol 93:45-52 (1999).

Mrak, R.E., et al., "Glial cytokines in Alzheimer's disease: review and pathogenic implications", Human Pathol 26 (8):816-23 (1995).

Neuman, M. et al., "Tumor Necrosis Factor Alpha and Apoptosis: Non-invasive Biomarkers for Diagnosis of Frontotemporal Lobar Degeneration and Alzheimer's Disease", First International Research Workshop on Frontotemporal Dementia in ALS, May 15-17, 2005, London, ON.

Öztürk, et al., "The diagnostic role of serum inflammatory and soluble proteins on dementia subtypes: Correlation with cognitive and functional decline", Behavioural Neurology 18(4):207-215 (2007).

Palmert, M. R. et al., "Soluble derivatives of the beta amyloid protein precursor in cerebrospinal fluid: alterations in normal aging and in Alzheimer's disease", Neurology 40, 1028-1034 (1990). (Abstract Only).

Pirtila, T. et al., "alpha1-Antichymotrypsin and IL-1beta are not Increased in CSF or Serum in Alzheimer's Disease", Neurobiology of Aging, vol. 15, No. 3, 313-317 (1994).

Rademakers, R. et al., "Advances in understanding the molecular basis of frontotemporal dementia", Nature Reviews: Neurology, vol. 8, 423-434 (2012).

Remarque, E.J., et al., "Patients with Alzheimer's disease display a pro-inflammatory phenotype". Experimental Gerontology 36:171-176 (2001).

Saas, P., et al. "CD95 (Fas/Apo-1) as a receptor governing astrocyte apoptotic or inflammatory responses: a key role in brain inflammation?", J Immunol. 162(4): 2326-2333 (1999).

Sajan, F.D. et al., "Apoptotic gene expression in Alzheimer's disease hippocampal tissue", American Journal of Alzheimer's disease and other dementias, Aug.-Sep. 2007, vol. 22, No. 4, p. 319-328 (2007).

(56) References Cited

OTHER PUBLICATIONS

Schmidt, R. et al., "Early Inflammatino and Dementia: A 25-Year Follow-up of the Honolulu-Asia Aging Study", Ann. Neurol. 52, 168-174 (2002).
Selkoe, D. J., "Cell biology of protein misfolding: the examples of Alzheimer's and Parkinson's diseases", Nature Cell Biology, vol. 6, No. 11, 1054-1061 (2004).
Sennvik, K. et al., "Levels of alpha- and beta-secretase cleaved amyloid precursor protein in the cerebrospinal fluid of Alzheimer's disease patients", Neuroscience Letters 278, 169-172 (2000).
Sjögren, M. et al., "Cytoskeleton proteins in CSF distinguish frontotemporal dementia from AD", Neurology 54(10), 1960-1964 (2000).
Sjögren, M. et al "Increased intrathecal inflammatory activity in frontotemporal dementia: pathophysiological implications". Journal of Neurology, Neurosurgery & Psychiatry, vol. 75, No. 8, p. 1107-1111 (2004).
Su, J. H. et al., "DNA damage and activated caspase-3 expression in neurons and astrocytes: evidence for apoptosis in frontotemporal dementia", Experimental Neurology, vol. 163, No. 1, p. 9-19 (2000).
Su, J.H. et al., "Fas and Fas Ligand are associated with neuritic degeneration in the AD brain and participate in beta-amyloid-induced neuronal death", Neurobiology of Disease, vol. 12, pp. 182-193 (2003).
Szczepanik, AM, et al., "IL-4, IL-10 and IL-13 modulate A beta(1—42)-induced cytokine and chemokine production in primary murine microglia and a human monocyte cell line", J Neuroimmunol, 113(1):49-62 (2001). (Abstract Only).
Takahashi, M., et al., "Immunoassay for Serum Glutamine Synthetase in Serum: Developmen, Reference Values, and Preliminary Study in Dementias", Clinical Chemistry 48, No. 2, 375-378 (2002).
Tan, et al., "Inflammatory markers and the risk of Alzheimer disease", Neurology 68(22):1902-1908 (2007).
Tanaka, J. et al., "Enzyme-linked immunosorbent assay for human autoantibody to glial fibrillary acidic protein: higher titer of the antibody is detected in serum of patients with Alzheimer's disease", Acta Neurol. Scand. 80, 554-560 (1989).
Tarkowski, E, et al., "Intracerebral production of tumor necrosis factor-alpha, a local neuroprotective agent, in Alzheimer's disease and vascular dementia". Journal of Clinical Immunology vol. 19, No. 4, 223-230 (1999).
Tohgi, H. et al., "Alterations of 3-nitrotyrosine concentration in the cerebrospinal fluid during aging and in patients with Alzheimer's disease", Neuroscience Letters 269, 52-54 (1999).
Wallin, A., et al., "Glial fibrillary acidic protein in the cerebrospinal fluid of patients with dementia", Dementia 7, 267-272 (1996). (Abstract Only).
Webster, S. et al., "Relative Efficacies of Amyloid Beta Peptide (A beta) Binding Proteins in A beta Aggregation", Journal of. Neuroscience Research 46, 58-66 (1996).
Webster, S. et al., "Molecular and Cellular Characterization of the Membrane Attack Complex, C5b-9, in Alzheimer's Disease", Neurobiology of. Aging, vol. 18, No. 4, 415-421 (1997).
Zighetti, M. L. et al., "Determination of total homocysteine in plasma: comparison of the Abbott IMx immunoassay with high performance liquid chromatography", Haematologica 87, 89-94 (2002).

\* cited by examiner

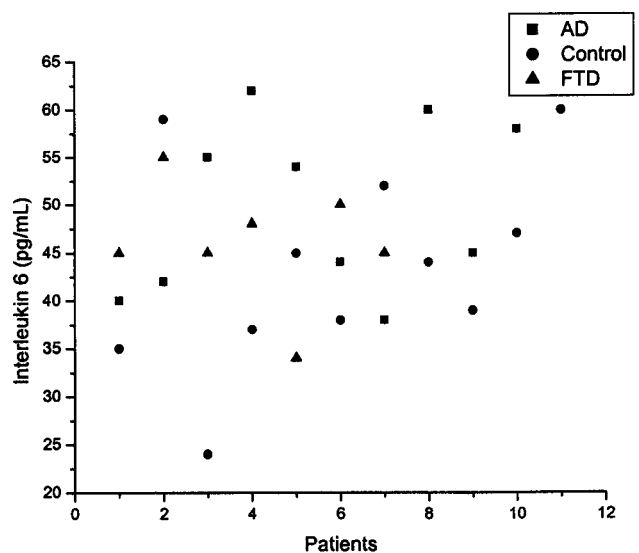
Figure 3.1
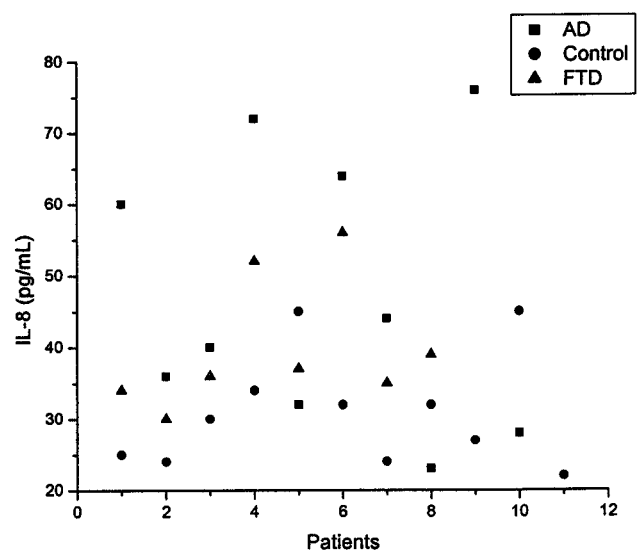
Figure 3.2

Table 1

| FTD Patient | Anatomical site of brain damage (imaging analysis) | Function impaired (neuropsychological assessment) | Biomarker Correlation |
|---|---|---|---|
| 1 | Orbital Frontal Gyrus (left) | Speech Language | TNF-α FasL |
| | Pre-Central Gyrus (left) | Concentration Attention Executive function | M-30 |
| 2 | Anterior Cingulate (ventral; left) | Executive function | TNF-α |
| | Posterior Cingulate (mid; left) | Executive function | IL8 M-30 |
| | Posterior Cingulate (right) | Executive function | M-30 |
| | Post Central Gyrus | | M-30 IL8 |
| 3 | Angular Gyrus (right) | Memory Anxiety | IL6 |
| | Mid-Temporal Gyrus (medial; right) | Attention Executive function | M-30 |
| | Superior Temporal Gyrus (lateral; right) | Attention Executive function | IL8 M-30 |
| | Temporal pole | | FasL |
| | Cuneus (left) | | TNF-α |
| 4 | Retro-Splenium (right) | | TNF-α |

Figure 4

Table 1.1

| Biomarker | Correlation with cognitive impairment |
|---|---|
| IL-6 | Last MMSE<br>Memory<br>Anxiety |
| IL-8 | Concentration<br>Attention<br>Executive |
| M-30 | Executive<br>Attention |
| FasL | Speech<br>Language |

Figure 4.1

TABLE 2 – Published biochemical markers proposed for AD and FTD in different body fluids and tissue

| Analyte | Body fluid | References |
|---|---|---|
| Aβ anti-bodies | Serum, plasma, CSF | Du, Y. et al.. Neurology 57, 801–805 (2001). |
| $α_1$-Anti-chymotrypsin | Blood, CSF | Abraham, C. R et al. Cell 52, 487–501 (1988).<br>Lanzrein, A. S. et al. Alzheimer Dis. Assoc. Disord. 12, 215–227 (1998).<br>Licastro, F et al. J. Neuroimmunol. 57, 71–75 (1995).<br>Pirttila, T et al. Neurobiol. Aging 15, 313–317 (1994). |
| Amyloid precursor protein (APP) | CSF | Henriksson, T. et al. J. Neurochem. 56, 1037–1042 (1991).<br>Palmert, M. R. et al. Neurology 40, 1028–1034 (1990).<br>Sennvik, K. et al. Neurosci. Lett. 278, 169–172 (2000).<br>Van Nostrand, W. E. et al. Proc. Natl Acad. Sci. USA 89, 2551–2555 (1992). |
| APP isoform ratio in platelets | Platelets | Baskin, F., et al. Neurology 54, 1907–1909 (2000).<br>Di Luca, M. et al.. Arch. Neurol. 55, 1195–2000 (1998).<br>Padovani, A. et al. Arch. Neurol. 59, 71–75 (2002). |
| β-Secretase (also known as BACE) | Platelets | Colciaghi, F. et al. Neurology 62, 498–501 (2004). |
| CD59 | Serum, plasma, CSF | Akiyama, H. et al. Neurobiol. Aging 21, 383–421 (2000). |
| C-reactive protein | Serum, plasma, CSF | Schmidt, R. et al. Ann. Neurol. 52, 168–174 (2002).<br>Licastro, F. et al. Alzheimer Dis. Assoc. Disord. 15, 51–55 (2001). |
| C1q | Serum, plasma, CSF | Smyth, M. D. et al. Neurobiol. Aging 15, 609–614 (1994).<br>Webster, S. & Rogers, J.. J. Neurosci. Res. 46, 58–66 (1996).<br>Webster, S. et al. Neurobiol. Aging 18, 415–421 (1997). |
| 8-hydroxy-deoxy-guanine | CSF, plasma, urine | Gabbita, S. P., et al. J. Neurochem. 71, 2034–2040 (1998).<br>Lovell M. A. & Markesbery, W. R.. Arch. Neurol. 58, 392–396 (2001). |
| Glutamine synthetase | Serum, CSF | Tumani, H., et al. Arch. Neurol. 56, 1241–1246 (1999).<br>Takahashi, M., et al. Clin. Chem. 48, 375–378 (2002). |

Figure 5A

TABLE 2 – Published biochemical markers proposed for AD and FTD in different body fluids and tissue

| | | |
|---|---|---|
| Glial fibrillary acidic protein (GFAP) and antibodies to GFAP | CSF | Wallin, A., et al. *Dementia* 7, 267–272 (1996).<br>Mecocci, P. *et al. J. Neuroimmunol.* 57, 165–170 (1995).<br>Tanaka, J. *et al. Acta Neurol. Scand.* 80, 554–560 (1989).<br>Terryberry, J. W., et al. *Neurobiol. Aging* 19, 205–216 (1998).<br>Hampel, H. *et al. Brain Res.* 823, 104–112 (1999). |
| Interleukin-6-receptor complex | Serum | Licastro, F. *et al. J. Neuroimmunol.* 103, 97–102 (2000). |
| Kallikrein | CSF, plasma | Diamandis, E. P., et al. *Clin. Biochem.* 33, 663–667 (2000). |
| Melanotransferrin | CSF, Serum | Zighetti, M. L., et al. *Haematologica* 87, 89–94 (2002). |
| Neurofilament proteins | CSF | Kennard, M. L., et al. *Nature Med.* 2, 1230–1235 (1996).<br>Feldman, H. *et al. J. Alzheimer Dis.* 3, 507–516 (2001).<br>Kim, D. K. *et al. Neuropsychopharmacology* 25, 84–90 (2001).<br>Sjogren, M. *et al. J. Neurosci. Res.* 66, 510–516 (2001).<br>Sjogren, M. *et al. Neurology* 54, 1960–1964 (2000).<br>Hu, Y. Y. *et al. Neurosci. Lett.* 320, 156–160 (2002). |
| Nitrotyrosine | CSF | Tohgi, H. *et al. Neurosci. Lett.* 269, 53–54 (1999).<br>Hensley, K. *et al. J. Neurosci.* 18, 8126–8132 (1998). |
| Oxysterols | Plasma, CSF | Hartmann, T. et al. *Trends Neurosci.* 24 (Suppl. 11), S45–S48 (2001). |
| Sulphatides | CSF 88,89 | Holtzman, D. M., et al. *Neurology* 58 (Suppl. 3), A361 (2002).<br>Han, X., et al. *J. Neurochem.* 82, 809–818 (2002). |
| Synaptic markers | Blood, CSF | Masliah, E. *Ann. NY Acad. Sci.* 924, 68–75 (2000).<br>Sheng, J. G. *et al. Neurobiol. Aging* 17, 359–363 (1996). |

Figure 5B

Table 3A: <u>NEUROPSYCHOLOGY BATTERY for AD</u>

1. Brief interview
2. KBNA Word list
3. KBNA Complex Figure
4. Trails A
5. Trails B
6. WAIS-III Digit Span
7. WAIS-III Digit Symbol – with incidental recall
8. (WASI Matrix Reasoning – if time)
9. KBNA Word list delayed recall
10. KBNA Word list recognition
11. KBNA Complex figure recall
12. KBNA Complex figure recognition
13. BNT – 30 items (odds or evens)
14. Fluency – CFL, animals, first names
15. WASI Vocabulary
16. WASI Similarities
17. WMS-R Logical Memory I – single story
18. KBNA Clocks (Free, Pre-drawn, Copy)
19. (WASI Matrix Reasoning, if not done earlier)
20. KBNA Sequences
21. D-KEFS Colour-Word Interference Test
22. Any other visuospatial tasks (Rey Copy, JLO)
23. WMS-R Logical Memory II - delayed recall
24. CCET
25. WCST – if doing
26. HADS

Figure 6A

Table 3B: <u>NEUROPSYCHOLOGY BATTERY for FTD</u>

1. Mattis DRS
2. CVLT-II/HVLT-R/KBNA – task given depends on capability of client
3. WMS (R or III) Logical Memory – version given depends on age of client
4. Rey-Osterrieth/KBNA (Copy, Immed, Delayed)
5. Trail-Making Test (Reitan/D-KEFS or Coloured)
6. WAIS-III Digit Span
7. WAIS-III Digit Symbol (with Incidental Recall)
8. Stroop Task (D-KEFS Colour-Word Interference Test)
9. Consonant Trigrams - if tolerated
10. FAS/CFL/BHR
11. Animals/Clothing, First names (girls, boys), Alternating Category
12. Boston Naming (full)
13. WRAT-3 Reading
14. WASI – at least Vocabulary and Matrix Reasoning; sometimes entire
15. WCST/64
16. Hayling Sentence Completion    }
17. Canadian Cognitive Estimations }    if necessary & possible
18. Gorham's Proverbs                       }
19. Go-No Go                                     }
20. SD/PPA
    WMS-III Face Recognition (if semantic dementia)
21. Token Test – I do a 16 item (Kimura) version
    Pyramid & Palm Trees        }
    PPVT-3                                    }    Usually done in S/L evaluation
22. Birmingham Object Recognition Battery – selected subtests
23. VOSP – selected subtests
24. Prosopagnosia Testing
25. BNT – multiple choice
26. WRAT-3 Spelling

Figure 6B

Table 4: Values for Biomarker Testing Kits. "val" is the value measured in the biomarker assay and is in pg/mL units for Fas-L and TNF-alpha.

| Example # | Biomarker | Assessment | Approximate thresholds |
|---|---|---|---|
| 1 | FAS-L (ng/mL) | Mild FTD | 70 < val < 80 |
| 2 | FAS-L (ng/mL) | Moderate FTD | 81 < val < 105 |
| 3 | FAS-L (ng/mL) | Severe FTD | 105 < val |
| 4 | FAS-L (ng/mL) | FTD + | 81 < val |
| 5 | FAS-L (ng/mL) | Abnormal; possible AD | 40 < val |
| 6 | TNF-alpha (pg/mL) | Possible AD | 80 < val |
| 7 | TNF-alpha (pg/mL) | Mild AD | 90 < val |
| 8 | TNF-alpha (pg/mL) | Moderate AD | 120 < val |
| 9 | TNF-alpha (pg/mL) | Severe AD | 140 < val |
| 10 | M-30 U/1000 mL | Very Likely FTD | 140 < val |
| 11 | M-30 U/1000 mL | Likely not AD | 140 < val |
| 12 | M-30 U/1000 mL | Likely FTD | 100 < val |
| 13 | M-30 U/1000 mL | Likely not FTD | 90 > val |
| 14 | FAS-L (ng/mL) | Likely FTD | Mean+2std (FAS-L level of sample AD group) <val |

Figure 7

| Component / Description | Quantity |
|---|---|
| BOX 1: Shipped on blue ice packs. Store at -20 °C. | |
| BOX 1A: Antigen Standards | One box of 12 1.5-ml tubes |
| BOX 1B: Detection Antibodies | One box of 12 1.5-ml tubes |
| Avidin-HRP Conjugate | One 1.5-ml tubes |
| 10% BSA | 15 ml bottle |
| Donkey Serum | 15 ml bottle |
| BOX 2: Shipped at ambient temperature. Store at 4 °C. | |
| 96-well pre-coated Capture Antibody microplate | One plate of 12 strips in a pouch |
| Detection Antibody Dilution Tube Strip | One strip of 12 tubes |
| Sample Dilution Buffer Stock | 60 ml bottle |
| Assay Buffer Stock | 60 ml bottle |
| Wash Buffer (10X Concentrate) | 125 ml bottle |
| Development Solution | 60 ml bottle |
| Stop Solution | 60 ml bottle |

Figure 8A

| Product Name | Human sAPO-1/Fas ELISA |
|---|---|
| Analyte | APO-1/Fas |
| Species | Human |
| Format | ELISA |
| Label | biotin-conjugate |
| Quantity / Tests / Concentration | 96 tests |
| Standard Range | 1000 - 15.6 pg/ml |
| Sample Volume | 10 µl |
| Incubation Time | 135 min |
| Sensitivity | xx pg/ml |

Figure 8B

1. Prepare replicate dilutions of samples.
2. Pipette 50 µl of Assay Buffer into each well of the 8-well ELISA strips.
3. Transfer 50 µl samples and/or standards to the appropriate wells of the ELISA strips.
4. Gently shake or tap plate for 10 s. Incubate for N seconds (where N depends upon the antibody) h at room temp.
5. Washing ELISA Wells: Decant or aspirate well contents. Add 350 µl 1X Washing Buffer. Gently shake or tap plate for 10 s. Decant or aspirate well content on absorbent paper to remove any residual buffer. Repeat wash twice more.
6. Pipette 100 µl of Detection Antibody solution. Incubate x h at room temp.
7. Wash ELISA wells as described above.
8. Add 100 µl Avidin-HRP solution to all wells. Incubate for 30 min at room temp.
9. Wash ELISA wells for a total of 4 washes.
10. Add 100 µl of Development Solution to each well. Incubate the plate for 15 min at room temp in the dark.
11. Add 100 µl of Stop Solution to each well. The colour changes.
12. Read absorbance at 450 nm within 30 min of stopping the reaction. If wavelength correction is available, subtract readings at 570 nm from the reading at 450 nm.

Figure 8C

|   | I/A-M30 | II-M30 | III-M30 | IV-IL6 | V-IL6 | VI-IL6 | VII-IL8 | VIII-IL8 | IX-IL8 | X-sFAS | XI-SFas | XII-sFAS |
|---|---|---|---|---|---|---|---|---|---|---|---|---|
| A | 1 | 9 | 17 | 25 | 33 | 41 | 49 | 57 | 65 | 73 | 81 | 89 |
| B | 2 | 10 | 18 | 26 | 34 | 42 | 50 | 58 | 66 | 74 | 82 | 90 |
| C | 3 | 11 | 19 | 27 | 35 | 43 | 51 | 59 | 67 | 75 | 83 | 91 |
| D | 4 | 12 | 20 | 28 | 36 | 44 | 52 | 60 | 68 | 76 | 84 | 92 |
| E | 5 | 13 | 21 | 29 | 37 | 45 | 53 | 61 | 69 | 77 | 85 | 93 |
| F | 6 | 14 | 22 | 30 | 38 | 46 | 54 | 62 | 70 | 78 | 86 | 94 |
| G | 7 | 15 | 23 | 31 | 39 | 47 | 55 | 63 | 71 | 79 | 87 | 95 |
| H | 8 | 16 | 24 | 32 | 40 | 48 | 56 | 64 | 72 | 80 | 88 | 96 |

Figure 9A

|   | I/A-M30 | II-M30 | III-M30 | IV-M30 | V-TNF-alpha | VI-TNF-alpha | VII-TNF-alpha | VIII-TNF-alpha | IX-sFas | X-SFAS | XI-SFas | XII-sFAS |
|---|---|---|---|---|---|---|---|---|---|---|---|---|
| A | 1 | 9 | 17 | 25 | 33 | 41 | 49 | 57 | 65 | 73 | 81 | 89 |
| B | 2 | 10 | 18 | 26 | 34 | 42 | 50 | 58 | 66 | 74 | 82 | 90 |
| C | 3 | 11 | 19 | 27 | 35 | 43 | 51 | 59 | 67 | 75 | 83 | 91 |
| D | 4 | 12 | 20 | 28 | 36 | 44 | 52 | 60 | 68 | 76 | 84 | 92 |
| E | 5 | 13 | 21 | 29 | 37 | 45 | 53 | 61 | 69 | 77 | 85 | 93 |
| F | 6 | 14 | 22 | 30 | 38 | 46 | 54 | 62 | 70 | 78 | 86 | 94 |
| G | 7 | 15 | 23 | 31 | 39 | 47 | 55 | 63 | 71 | 79 | 87 | 95 |
| H | 8 | 16 | 24 | 32 | 40 | 48 | 56 | 64 | 72 | 80 | 88 | 96 |

Figure 9B

|   | I/A-TNF-alpha | II-TNF-alpha | III-TNF-alpha | IV-IL6 | V-IL6 | VI-IL6 | VII-IL8 | VIII-IL8 | IX-IL8 | X-sFAS | XI-SFas | XI sFAS |
|---|---|---|---|---|---|---|---|---|---|---|---|---|
| A | 1 | 9 | 17 | 25 | 33 | 41 | 49 | 57 | 65 | 73 | 81 | 89 |
| B | 2 | 10 | 18 | 26 | 34 | 42 | 50 | 58 | 66 | 74 | 82 | 90 |
| C | 3 | 11 | 19 | 27 | 35 | 43 | 51 | 59 | 67 | 75 | 83 | 91 |
| D | 4 | 12 | 20 | 28 | 36 | 44 | 52 | 60 | 68 | 76 | 84 | 92 |
| E | 5 | 13 | 21 | 29 | 37 | 45 | 53 | 61 | 69 | 77 | 85 | 93 |
| F | 6 | 14 | 22 | 30 | 38 | 46 | 54 | 62 | 70 | 78 | 86 | 94 |
| G | 7 | 15 | 23 | 31 | 39 | 47 | 55 | 63 | 71 | 79 | 87 | 95 |
| H | 8 | 16 | 24 | 32 | 40 | 48 | 56 | 64 | 72 | 80 | 88 | 96 |

Figure 9C

METHODS AND KITS FOR THE DIFFERENTIAL DIAGNOSIS OF ALZHEIMER'S DISEASE VERSUS FRONTOTEMPORAL DEMENTIA AND FOR THE DIAGNOSIS OF FRONTOTEMPORAL DEMENTIA, COMPRISING FAS-L AND CK 18 AS BIOMARKERS

This application is a continuation application of U.S. patent application Ser. No. 12/922,775, filed Sep. 15, 2010, now abandoned which is a §371 Application of PCT/CA09/00346, filed 20 Mar. 2009, which in turn claims priority to U.S. Provisional application 61/038,475 filed 21 Mar. 2008. Each of the foregoing applications is incorporated by reference herein.

FIELD OF THE INVENTION

The invention relates to systems and methods for using serum biomarkers to assess and/or discriminate between patients suffering from Alzheimer's disease (AD), and patients with AD-like disorders demonstrating cognitive features similar to features of AD and normal aging individuals.

BACKGROUND

AD is a progressive neurodegenerative disease with increasing incidence as the population lives longer and longer. Between 1980 and 2000, the number of Americans diagnosed with AD more than doubled with current estimates of about 24 million people worldwide. AD usually occurs in people over 65 years old and is the most common cause of dementia in adults, gradually destroying a person's memory and ability to learn, reason, make judgments, communicate and carry out daily activities. In later stages, patients may experience changes in personality and behavior, such as anxiety, suspicion, agitation and aggression. Delusions and hallucinations may also occur. The average life expectancy is approximately seven years.

Presently, the only way to diagnose AD with certainty is by autopsy. However, a clinical diagnosis of AD is typically determined through a series of evaluations in patients presenting with memory loss and other features of cognitive decline. The diagnostic workup includes a medical history, general physical and neurological examination, and administration of a cognitive test battery to assess mental function. The cognitive test battery often includes standardized cognitive screening tests such as the Mini-Mental State Examination (MMSE). A patient's cognitive test battery results are often considered in combination with existing clinical information and laboratory test results to assess the patient. Upon reaching a diagnosis of AD, a physician will further classify the disease as mild (early stage), moderate, or severe (late stage).

The defining lesions of AD are neurofibrillary tangles (NFTs) and senile plaques formed by neuronal accumulations of abnormal tau protein filaments and extracellular deposits of A-fibrils, respectively, both of which are implicated in mechanisms of AD brain degeneration. On the other hand, frontotemporal dementia (FTD) is associated with a broad spectrum of pathologies that may be characterized by abnormalities in tau, as well as ubiquitin positive inclusions. The early diagnosis of disorders such as FTD and AD, when therapy is likely to have the greatest impact, may be beneficial. The benefit may extend to monitoring patient responses to new therapeutic interventions in clinical trials. Biomarkers can also assist in overcoming some of the obstacles presented by the complexity of neurodegenerative diseases which are exemplified by neuro-degenerative tauopathies, a number of which overlap, since the biomarkers can provide objective surrogate markers of the disease and disease severity.

Improved means of diagnosing AD earlier and more accurately are required. Ultimately, there is a need for a reliable, valid, inexpensive, and early diagnostic test that can be used in any doctor's office.

There is evidence suggesting inflammation as a factor in the pathogenesis of AD. Research has been conducted to evaluate the potential of IL-1β, IL2, IL6, IL12, IL18 and TNF-α as biomarkers of AD and as a means to distinguish AD from other dementias (Guerreiro et al. (2007) *Neurodegenerative Disease* 4(6):406-412; Ozturk at al. (2007) *Behavioural Neurology* 18(4):207-215; Tan et al. (2007) *Neurology* 68(22):1902-1908). The data suggested higher levels of TNF-α and other pro-inflammatory cytokines could be predictive of risk of AD and could be used to assist in the diagnosis of AD.

In response to a peripheral infection, innate immune cells produce pro-inflammatory cytokines that act on the brain to cause sickness of the brain followed by a change in behaviour. When activation of the peripheral immune system continues, such as during systemic infections, autoimmune diseases, or chronic illness, the immune signalling to the brain can lead to an exacerbation of sickness and the development of symptoms. There is a body of evidence that inflammatory mediators may contribute to changes in brain. The first demonstration that peripherally administered bacterial toxin, lipopolysaccharide (LPS) induces the expression of interleukin (IL)-1β in the brain of rats (van Dam et al., 1992). This article was followed by many studies looking in mice, rats and human cells in vitro expose to LPS (Laye et al. 1994; Lombardi et al., 1999; Dziedzica et al., 2003) or stimulated with beta-amyloid that produce different cytokines (DelBo et al., 1995; Blasko et al., 1999; Meda et al. 1999). Tumor necrosis factor alpha, TNF-α- and IL-1β-induced sickness behaviour was observed (Huberman et al., 1994; Benveniste et al., 1999) in cells in vitro. Frohman et al., (1991) described expression of intercellular adhesion molecule 1 (ICAM-1) in AD. These data are consistent with the idea that in the brain, as in systemic organs, the natural balance between pro- and anti-inflammatory cytokines regulates the intensity and duration of the response to immune stimuli in patients with AD predisposing them to a pro-inflammatory phenotype (Akiyama et al., 2000; Remarque et al., 2001). There are studies that identify cytokines (transforming growth factor beta-TGF-beta (Chao et al., 1994; Flanders et al. 1995), intercellular adhesion molecule 1 (ICAM-1) (Frohman et al., 1991), Vascular endothelial factor (VEGF) elevated in serum of patients with vascular dementia. There is, however, a need for biomarkers that differentiate between AD and FTD.

A number of groups have identified novel biomarkers of AD and AD-like disorders and methods for assessment of AD and AD-like disorders. US Patent Application Publication No. 2007/0042429 describes a biomarker assay for differentiating between AD and AD-like disorders which utilizes 2-dimensional gel electrophoresis. Gel electrophoresis is also described in International Patent Application Publication No. WO/2004/001421 as a method for diagnosis and differential diagnosis of mental disorders.

US Patent Application Publication No. 2007/0037200 describes methods and compositions for diagnosing, stratification, and monitoring of AD and other neurological disorders as reflected in various body fluids.

Potential biomarkers of AD are disclosed in International Patent Application Publication Nos. WO05/052592, WO06/

133423, WO06/028586, WO05/047484, WO06/113289, WO04/019043, and WO06/003414.

While AD is the most common type of dementia accounting for 60-80% of all cases of dementia, other causes of dementia may manifest similarly. One such AD-like disorder is frontotemporal dementia (FTD), which accounts for as many as 20% of dementias presenting under age 65. Because of its symptoms, FTD is commonly diagnosed as AD. FTD affects the frontal and temporal lobes of the brain and is associated with more rapid onset compared to AD. The frontotemporal lobar neuronal degeneration observed in FTD patients is believed to be associated with apoptosis events precipitated by activated macrophages and astrocytes.

FTD and AD are neurological disorders characterized by anterior and posterior brain damage, respectively. The differences in neuroanatomical structures affected by the disorders may also reflect different biomarker profiles. In FTD, products of activated macrophages and astrocytes lead to central nervous system dysfunction by directly damaging neurons by induction of altered gene and protein expression profiles. Inflammation corresponding to AD is primarily due to elevated levels of pro-inflammatory cytokines, the main cytokine being tumor necrosis factor alpha (TNF-α).

Despite the numerous differences between FTD and AD, there is overlap in clinical presentation. For example, Binetti et al. (Arch Neurol (2000) 57:225-232) reported findings in 121 patients with AD and 44 patients with Pick's disease (i.e., FTD). The authors showed that cognitive test performance did not clearly distinguish between the two groups. In addition, patients with AD can have behavioural changes suggestive of frontal lesions, such as apathy and euphoria, although these abnormalities are more prominent in FTD. Despite similarities between FTD and AD, such as those found by Binetti et al., the two are separate disease entities.

AD differs from FTD in neuropathology, neurochemistry, genetics, distribution of lesions, and clinical presentation. The histopathology is distinct from FTD and includes neuritic plaques, neurofibrillary tangles, loss of synapses and neurons, granulovacuolar degeneration, AMY plaques, and amyloid angiopathy. In addition, there is a prominent cholinergic deficit in AD with a marked and consistent deficiency in choline acetyltransferase and acetylcholine synthesis (Arriagada P V, Growdon J H, Hedley-Whyte E T, Hyman B T. Neurofibrillary tangles but not senile plaques parallel duration and severity of Alzheimer's disease. Neurology 1992; 42(3):631-639), whereas there is no cholinergic deficit in FTD (Hof et al. Arch Neurol (1992) 49:946-953). At least 4 genes with loci on chromosomes 1, 14, 19, and 21, respectively, have been linked to AD (Mathuranath et al. Neurology (2000) 55:1613-1620), whereas mutations on chromosome 17 have been related to FTD (Bird et al. Neurobiol Aging (2001) 22:113-114). Also in contrast to FTD is the distribution of pathological changes in AD, which involve primarily posterior brain structures, as opposed to anterior brain damage in FTD (Neary D. Frontotemporal degeneration, Pick disease, and corticobasal degeneration. One entity or 3? Arch Neurol 1997; 54:1425-1426).

In addition to the above, there are striking clinical differences between AD and FTD (Nearye et al. Arch Neurol (1997) 54:1425-1426). These include preserved ability to interact well at an interpersonal level and preservation of social graces, manners and courtesy until late in AD versus early and prominent decline in social interpersonal conduct in FTD. There is also early and pervasive memory loss, spatial disorientation, and aphasia in AD whereas in FTD memory loss is variable and is never the dominating feature, visuospatial function is preserved, and language is characterised by adynamic speech. Hodges et al. (Neuropsychology (1999) 13(1):31-40) presented differences between FTD and AD. This difference was based largely upon a lack of impairment in FTD on neuropsychological measures compared to impaired performance in AD. Thus, FTD and AD are distinctly different disorders and are well-suited as models of anterior and posterior dementias.

There remains a need to identify biomarkers that distinguish between AD and AD-like disorders such as FTD, especially as there are therapies that are recommended for AD but do not work in FTD (Binetti G, Locascio J J, Corkin S, Vonsattel J P, Growdon J H. Differences between Pick disease and Alzheimer disease in clinical appearance and rate of cognitive decline. Arch Neurol 2000; 57:225-232). Identification of such biomarkers will provide a means to assist diagnosis, enabling earlier and more relevant treatment interventions.

SUMMARY OF THE INVENTION

In one aspect, there is provided a method for the differential diagnosis in an individual of Alzheimer's disease (AD) versus frontotemporal dementia (FTD), said method comprising:
  a) obtaining a biological sample from said individual,
  b) measuring levels of TNF-α, FAS-L, and caspase-cleaved CK18 in said biological sample,
  c) comparing the levels determined in (b) to reference levels for each of said TNF-α, FAS-L and caspase-cleaved CK18 to determine whether the individual is suffering from AD or FTD.

In another aspect, step (c) further comprises comparing the levels of TNF-α, FAS-L and caspase-cleaved CK18 determined in (b) to reference levels for each of said TNF-α, FAS-L and caspase-cleaved CK18 relating to severity of AD or FTD to assess the severity of AD or FTD in said individual.

In another aspect, there is provided a method for the diagnosis of frontotemporal dementia (FTD) in an individual, said method comprising:
  a) obtaining a biological sample from said individual,
  b) measuring levels of FAS-L and caspase-cleaved CK18 in said biological sample,
  c) comparing the levels determined in (b) to reference levels for each of said FAS-L and caspase-cleaved CK18 to determine whether the individual is suffering from FTD.

In yet another aspect, there is provided a method for assessing the severity of frontotemporal dementia (FTD) in an individual, said method comprising:
  a) obtaining a biological sample from said individual,
  b) measuring levels of FAS-L and/or caspase-cleaved CK18 in said biological sample,
  c) comparing the levels determined in (b) to reference levels for each of said FAS-L and/or caspase-cleaved CK18 relating to severity of FTD to assess the severity of FTD in said individual.

In still yet another aspect, there is provided a method of monitoring progression of FTD in a patient previously diagnosed with FTD comprising:
  a) obtaining a biological sample from said individual,
  b) measuring levels of FAS-L and/or caspase-cleaved CK18 in said biological sample,
  c) comparing the levels determined in (b) to reference levels for each of said FAS-L and/or caspase-cleaved CK18.

In one aspect, the reference levels are levels of said FAS-L and/or caspase-cleaved CK18 obtained from a biological sample from the same FTD patient at an earlier point in time.

In yet another aspect, there is provided a diagnostic kit for determining a differential diagnosis in an individual of Alzheimer's disease (AD) versus frontotemporal dementia (FTD) comprising:
 a) reagents specific for TNF-α, FAS-L, and caspase-cleaved CK18,
 b) instructions for use of the reagents to determine levels of said TNF-α, FAS-L, and caspase-cleaved CK18 in biological samples obtained from an individual.

In another aspect, there is provided a diagnostic kit for detecting frontotemporal dementia (FTD) in an individual comprising:
 a) reagents specific for FAS-L and caspase-cleaved CK18,
 b) instructions for use of the reagents to determine levels of said FAS-L and caspase-cleaved CK18 in biological samples obtained from an individual.

BRIEF DESCRIPTION OF THE DRAWINGS

FIG. 3.1 is a scatter plot of the levels of IL-6 in the sera of patients with AD (squares), FTD (triangles), control patients (circles), illustrating that no statistical significance is observed between the individuals in different groups. IL-6 levels in 7 FTD patients (triangles); 10 AD patients (squares) and 11 controls (circles).

FIG. 3.2 is a scatter plot of the levels of IL-8 in the sera of patients with AD (squares), FTD (triangles), control patients (circles), illustrating that no statistical significance is observed between the individuals in different groups.

FIG. 4 is a table indicating relationships between biomarkers, SPECT imaging, and neuropsychological assessment data for four FTD subjects.

FIG. 4.1 is a table indicating correlation between cognitive deficit and biomarker.

FIGS. 5A-B are published biochemical markers proposed for AD and FTD in different body fluids and tissue.

FIG. 6A is a table listing a series of neuropsychological tests used in a test battery to assess AD.

FIG. 6B is a table listing a series of neuropsychological tests used in a test battery to assess FTD.

FIG. 7 is a table of proposed reference values for biomarkers FAS-L, TNF-α, and caspase-cleaved cytokeratin 18 (CK18) as detected by M-30.

FIG. 8A: shows a parts list of components included in 2 types of testing kits.

FIG. 8B: shows an example of an information sheet included with a testing kit.

FIG. 8C: shows an additional example of an information sheet to be included with a testing kit.

FIG. 9A: is a diagrammatic illustration of an example testing kit that can be used to detect FTD and it can also be used to assess measures relating to the severity of the disease.

FIG. 9B: is a diagrammatic illustration of an example testing kit that can be used to differentially diagnose between AD and FTD, as well as assess the severity of AD and FTD.

FIG. 9C: is a diagrammatic illustration of an example testing kit that can be used to detect AD and it can also be used to assess measures relating to the severity of the disease.

DETAILED DESCRIPTION

Figure 1:
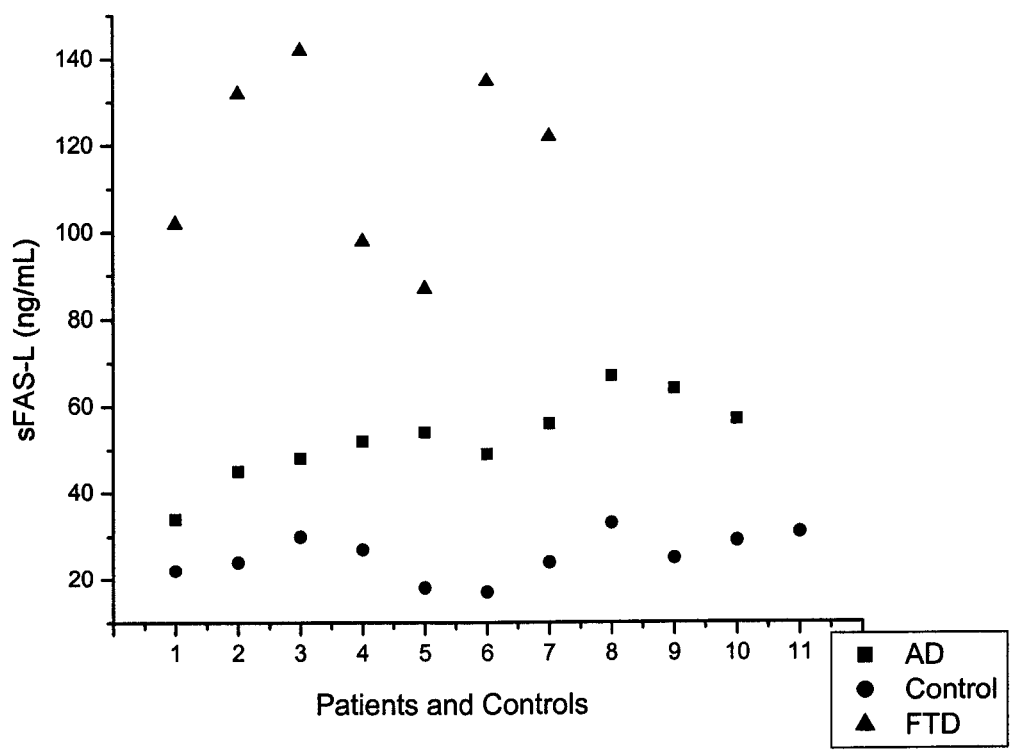
FIG. 1 is a scatter plot of the levels of FAS-L in the sera of patients with AD (squares), FTD (triangles), and control patients (circles), further indicating statistically significant ($p<0.001$) elevation of Fas-L levels in FTD compared to AD and controls. The scatter plot shows the values of sFAS-L (ng/mL) in sera of the patients with AD (10—squares), Control Patients (11—Circles) and FTD (7—Triangles). sFas is statistically higher in FTD ($p<0.001$) when compared to AD and to controls. sFas is statistically higher in AD ($p<0.001$) when compared to controls.

In one embodiment, protein biomarkers that are differentially expressed in subjects having Alzheimer's Disease, AD-related disorders, and normal individuals are provided. The biomarkers are a combination of inflammation and apoptosis biomarkers. In particular, an assay to determine levels of inflammatory biomarkers and apoptosis biomarkers is provided. More particularly, methods of using TNF-α, IL6 and IL8 as biomarkers of inflammation and FAS-L and caspase-cleaved cytokeratin 18 (CK18) (detected by M-30 antibody) as biomarkers of apoptosis are provided.

In one embodiment, there is provided a method for the differential diagnosis in an individual of Alzheimer's disease (AD) versus frontotemporal dementia (FM), said method comprising:
 a) obtaining a biological sample from said individual,
 b) measuring levels of TNF-α, FAS-L, and caspase-cleaved CK18 in said biological sample,
 c) comparing the levels determined in (b) to reference levels for each of said TNF-α, FAS-L and caspase-cleaved CK18 to determine whether the individual is suffering from AD or FTD.

In another embodiment, step (c) further comprises comparing the levels of TNF-α, FAS-L and caspase-cleaved CK18 determined in (b) to reference levels for each of said TNF-α, FAS-L and caspase-cleaved CK18 relating to severity of AD or FTD to assess the severity of AD or FTD in said individual.

In other embodiments:
 a measured level of TNF-α of from about 80 pg/mL to about 90 pg/mL is indicative of possible AD;
 a measured level of TNF-α of from about 90 pg/mL to about 120 pg/mL is indicative of mild AD;
 a measured level of TNF-α of from about 120 pg/mL to about 140 pg/mL is indicative of moderate AD; and
 a measured level of TNF-α of from greater than about 140 pg/mL is indicative of severe AD.

In still other embodiments:
 a measured level of FAS-L of from about 70 pg/mL to about 80 pg/mL is indicative of mild FTD;
 a measured level of FAS-L of from about 81 pg/mL to about 105 pg/mL is indicative of moderate FTD; and a measured level of FAS-L greater than 105 pg/mL is indicative of severe FTD.

In another embodiment, a measured level of caspase-cleaved CK18 above 100 U/1000 mL is indicative of FTD.

In yet another embodiment, there is provided a method for the diagnosis of frontotemporal dementia (FTD) in an individual, said method comprising:
 a) obtaining a biological sample from said individual,
 b) measuring levels of FAS-L and caspase-cleaved CK18 in said biological sample,
 c) comparing the levels determined in (b) to reference levels for each of said FAS-L and caspase-cleaved CK18 to determine whether the individual is suffering from FTD.

In another embodiment, there is provided a method for assessing the severity of frontotemporal dementia (FTD) in an individual, said method comprising:
 a) obtaining a biological sample from said individual,
 b) measuring levels of FAS-L and/or caspase-cleaved CK18 in said biological sample,
 c) comparing the levels determined in (b) to reference levels for each of said FAS-L and/or caspase-cleaved CK18 relating to severity of FTD to assess the severity of FTD in said individual.

In yet another embodiment, there is provided a method of monitoring progression of FTD in a patient previously diagnosed with FTD comprising:
 a) obtaining a biological sample from said individual,
 b) measuring levels of FAS-L and/or caspase-cleaved CK18 in said biological sample,
 c) comparing the levels determined in (b) to reference levels for each of said FAS-L and/or caspase-cleaved CK18.

In another embodiment, the reference levels are levels of said FAS-L and/or caspase-cleaved CK18 obtained from a biological sample from the same FTD patient at an earlier point in time.

In still another embodiment, there is provided a diagnostic kit for determining a differential diagnosis in an individual of Alzheimer's disease (AD) versus frontotemporal dementia (FTD) comprising:
 a) reagents specific for TNF-$\alpha$, FAS-L, and caspase-cleaved CK18,
 b) instructions for use of the reagents to determine levels of said TNF-$\alpha$, FAS-L, and caspase-cleaved CK18 in biological samples obtained from an individual.

In another embodiment, the diagnostic kit further comprises a reference substance for each of said TNF-$\alpha$, FAS-L, and caspase-cleaved CK18 for normalizing data. In other embodiments, the diagnostic kit further comprises an information sheet for comparing measured levels of said TNF-$\alpha$, FAS-L, and caspase-cleaved CK18 to reference levels for each of said TNF-$\alpha$, FAS-L, and caspase-cleaved CK18 to determine whether said individual is suffering from AD or FTD, and/or an information sheet for comparing the levels of TNF-$\alpha$, FAS-L and caspase-cleaved CK18 to reference levels for each of said TNF-$\alpha$, FAS-L and caspase-cleaved CK18 relating to severity of AD or FTD to determine the severity of AD or FTD in said individual.

In yet another embodiment, there is provided a diagnostic kit for detecting frontotemporal dementia (FTD) in an individual comprising:
 a) reagents specific for FAS-L and caspase-cleaved CK18,
 b) instructions for use of the reagents to determine levels of said FAS-L and caspase-cleaved CK18 in biological samples obtained from an individual.

In another embodiment, the diagnostic kit further comprises a reference substance for each of said FAS-L and caspase-cleaved CK18 for normalizing data. In still another embodiment, the diagnostic kit further comprises an information sheet for comparing the levels of FAS-L and caspase-cleaved CK18 to reference levels for each of said FAS-L and caspase-cleaved CK18 relating to severity of FTD to determine the severity of FTD in said individual.

In another embodiment, the biological sample is a blood sample. In another embodiment, the blood sample may be a peripheral blood sample.

FIGS. 5A and 5B illustrate published (prior art) biochemical markers proposed for AD and FTD in different body fluids and tissue.

It is known that AD correlates with a high degree of inflammation in certain regions of the brain (Akiyama et al. (2000) Neurobiol Aging 21(3):383-421).

Biomarkers of inflammation in AD include IL6 and IL8. IL6 is both a marker of inflammation and regeneration, correlating with earlier stages of the inflammatory process. Elevated levels of IL6 are indicative of early inflammatory processes. Elevated IL8 levels are indicative of a later stage in inflammation, and play a role in signalling neutrophils to enter the site of damage. Similar to IL8, RANTES levels are associated with higher degrees of inflammation and more advanced stages of the inflammatory process. In this regard, IL8 and RANTES levels are indicative of progressive inflammation compared to IL6. In this regard, measuring levels of each of IL6, IL8 and RANTES is useful in staging the inflammatory process which correlates with stage of disease.

It has been suggested that astrocytes are primed by IL-8 in vitro to produce inflammation and that Fas is producing apoptosis of this type of brain cells (Bernard D, Walker P R, Dietrich P Y. CD95 (Fas/Apo-1) as a receptor governing astrocyte apoptotic or inflammatory responses: a key role in brain inflammation?: J Immunol. 1999 Feb. 15; 162(4): 2326-33.)

TNF-$\alpha$ is a well known marker of inflammation. However, it has also been shown to induce cell death. The high degree of inflammation in AD results in necrotic cell death, in contrast to apoptotic cell death observed in other AD-related disorders including FTD.

The elevated levels of apoptosis in FTD subjects compared to AD subjects suggested apoptosis biomarkers as potentially useful in distinguishing between AD and FTD. Useful markers of apoptosis include (i) caspase-cleaved cytokeratin 18 (CK18) in CK18 positive cells which is specifically detected by M-30 monoclonal antibody (the M-30 monoclonal antibody does not bind to uncleaved CK18), and (ii) FAS-L, a well known apoptotic factor that is induced by elevated TNF-$\alpha$ levels. In particular, these proteins are markers of mitochondrial apoptosis processes.

FAS-L may also be referred to using a number of synonymous names such as: Apoptosis antigen 1; Apoptosis mediating surface antigen FAS; CD95 antigen; and, Tumor necrosis factor receptor superfamily 6. The sFas unit contains a family of proteins that can be used to assess mitochondrial functions, which occur during apoptotic responses.

Caspase-cleaved cytokeratin 18 (CK18) as measured by M-30 monoclonal antibody is proposed to be a surrogate biomarker of different mechanisms of cell death by apoptosis. During apoptosis intermediate filament proteins (including CK18) are targeted for rapid breakdown by activated caspases 3, 7 and 9 to facilitate the formation of apoptotic bodies. Nonetheless, the fragments of CK18 produced by proteolysis are stable and persist as large aggregates eventually appearing in the circulation.

Mitochondria evolved as specialized organelles with a plethora of cellular functions. They not only house the respiratory chain and provide cellular energy but are also the site of essential biosynthetic pathways. Mitochondria serve as calcium stores and are integrated in a number of signalling pathways, including cell death cascades, thus controlling cellular homoeostasis in multiple ways. Dysfunction of mitochondria has severe cellular consequences and is linked to neuro-degeneration in humans, including FTD and AD.

Several surveillance strategies have evolved that limit mitochondrial damage and ensure cellular integrity. Intraorganellar proteases conduct protein quality control and exert regulatory functions detecting the damage and initiating the process of apotosis (cleaved caspase 8 and Fas), membrane fusion and fission allow mitochondria within a cell to respond to signals and produce effector decisions in apoptosis (cleaved caspase 3 and cytokeratine 18), and the autophagic degradation of severely damaged apoptotic cells protects against inflammation and further damage.

In this work we applied the current knowledge on these surveillance strategies and their role in AD and FTD. We analyzed 2 different markers of apoptosis that are acting in different points in time in the process of apoptosis. FasL is one of the $17^{th}$ members of the TNF superfamily. The TNF superfamily of cytokines includes both soluble and membrane bound proteins that regulate cellular activation. FasL/TNFSF6 (fas Ligand, CD95-ligand, ligand APO) is responsible for signaling for apoptosis in the cell. M-30 or cleaved cytokeratine 18 comes into the apoptotic cascade after the FasL and caspase 8 have already given the signal that the cell should commit suicide. At this point, the effector caspase 3 has been cleaved already and the cytokeratine 18 can therefore be detected in the blood stream.

Thus, FAS signaling is involved in early apoptotic events (initiation) whereas cleavage of CK18 (detected by M-30 antibody) is a marker of apoptosis execution stage (considering an apoptosis process that progresses as 1) initiation; 2) execution; and 3) burial). In this regard, the two markers represent different stages of apoptosis.

By analyzing both caspase-cleaved cytokeratin 18 (CK18) and FAS-L levels, it is expected that the sensitivity and/or specificity of diagnosis of FTD, as well as assessing the severity and progression of FTD, will be enhanced in light of the foregoing.

The non-invasive biomarkers described herein can be used to objectively distinguish between various types of dementia. Most particularly, this was explored with respect to FTD and AD which can be seen as representing models of anterior and posterior dementia, respectively. Accordingly, biomarker correlates of these disorders are believed to reflect, in part, the different neuroanatomical subsystems, which are targeted by these two disorders. Biomarkers were therefore selected in relation to brain structure and function in the context of dementia. This approach has been poorly studied and addressed by previous investigators. The success of these biomarkers represents a significant advance in defining the clinical manifestations of dementia. Moreover, the diagnosis of clinical and objective biochemical markers should greatly benefit the detection, assessment, diagnosis, quantification of the disorder and also improve the therapy of patients. The ELISA Kits can be used to distinguish between control normal individuals, AD, and FTD diseases, or to assist with medical research in this area.

Accordingly, methods are provided of assessing AD and AD-related disorders by measuring the levels of inflammation and apoptosis biomarkers in an individual and comparing the measured levels to reference levels. In this regard, higher than normal levels of inflammatory biomarkers in conjunction with normal or near normal levels of apoptosis biomarkers is suggestive of AD, whereas normal or near normal levels of inflammatory markers and elevated levels of apoptotic markers are suggestive of FTD.

Enzyme-Linked ImmunoSorbent Assay (ELISA) can be used to detect the presence of an antibody or an antigen (biomarker level) in a biological sample. Alternatively, Enzyme ImmunoAssay (EIA) can be used to determine biomarker levels. The ELISA tests can include variations known to those of skill in the art. The kits can be adopted to use fluorescence or chromogenic ELISA, direct and indirect ELISA methods, competitive ELISA and "sandwich" ELISA methods. Competitive ELISA can be used that employ enzyme-linked antigen rather than enzyme-linked antibody. Those of skill in the art will recognize that other affinity-based technologies may be used in the methods described herein.

In one embodiment, there is provided a method of distinguishing between AD and AD-related disorders, particularly FTD.

In one embodiment, there is provided a method for determining the risk of developing AD or an AD-related disorder. The status of a subject may be low, medium, or high risk based of calculated levels of biomarkers. The amounts of the individual biomarkers or patterns of biomarker levels are characteristic of risk state (e.g. low, medium, or high). The risk of developing AD or AD-related disease is determined by measuring relevant biomarker levels in a subject and comparing the levels with a reference level or pattern of biomarker levels associated with a specific level of risk.

In one embodiment, there is provided a method for determining the stage of AD of AD-related disorder. Each stage (e.g., early, mid, and late) is associated with a characteristic amounts of each biomarker (a pattern). The stage of disease is determined by measuring the levels of the biomarkers and comparing them with reference amounts associated with a particular stage of disease. For example, biomarker levels can be used to classify between early stage AD and non-AD.

In one embodiment, there is provided a method for determining the course of disease in a subject. Disease course refers to changes in disease status over time, whether progressive (worsening) or regressive (improving). Over time, levels in biomarkers may change. For example, increasing amounts of TNF-α are associated with progression of AD while increasing amounts of FAS-L are associated with progression of FTD.

In one embodiment, there is provided a kit for assessing levels of biomarkers of apoptosis and biomarkers of inflammation. For example, a test may yield a FTD score wherein both caspase-cleaved cytokeratin 18 (CK18) as detected by M-30 and Fas-L are positively correlated, and the likelihood of FTD increases with increased measures of M-30 and FAS-L levels.

Similarly, an AD score can be obtained. In one embodiment, M-30 is negatively correlated and TNF-α is positively correlated. The AD score will increase as the M-30 decreases and TNF-α increases. Information about more than one biomarker can be used to provide a two-step confirmation of a test score. For example, caspase-cleaved cytokeratin 18 (CK18) as detected by M-30 must be below a first specified threshold and TNF-α must be above a second specified threshold in order for the test score to indicate that the patient is positively identified as AD.

By "AD-related disorder" is meant any one of a number of disorders having associated with it presenting symptoms similar to those of AD. AD-related disorders include mild cognitive impairment (MCI), vascular dementia, mixed dementia, dementia with Lewy bodies, Parkinson's Disease, Creutzfeld-Jakob Disease, Huntington's Disease, and Frontotemporal Dementia (FTD).

By "biomarker" is meant any assayable characteristic or composition that can be used to identify a condition (e.g., a neurodegenerative disease or lack thereof) or the status of a condition in a subject or sample. A biomarker can, in some examples disclosed herein, be a protein whose expression characteristics can be used to identify a condition or status of a condition in a subject or sample.

By "biological sample" is meant any one of a number of biological samples obtained from an individual for use in a diagnostic or monitoring assay. The definition encompasses blood, cerebral spinal fluid (CSF), urine and other liquid samples of biological origin.

By "peripheral biological sample" is meant a biological sample that is not derived from the central nervous system (i.e., not a CSF sample) and includes blood samples and other biological samples not derived from the CNS.

By "blood sample" is meant a biological sample which is derived from blood, preferably, peripheral blood. A blood sample may be, for example, whole blood, plasma or serum.

By "normal" individual or sample from an individual is meant an individual or sample from an individual assessed as not having AD or an AD-related disorder, and has a MMSE score or would achieve a MMSE score within the range of 25-30.

By "reference level" is meant a level of biomarker concentration in a sample against which a test sample from a subject is compared. The reference level may be one of that associated with a normal, non-demented individual or may be a level determined for an individual earlier in the course of diagnosis. Regarding the latter, the reference level is useful to determine changes in biomarker levels which are indicative of disease progression.

By "normal serum level" is meant a level of biomarker in a sample that is within a range present in individuals not affected by AD or AD-related disorders. Normal serum levels are determined from concentrations present in normal, unaffected individuals.

By "stage of disease" is meant the severity of the disease classified largely as one of mild (early stage), moderate (midstage), or severe (late stage). A determination of stage of disease is important in planning treatment, or proposing treatment options.

Example 1

Patients

Twenty-eight subjects in total were recruited for the study. The subjects represented three distinct groups: FTD (n=7), AD (n=10), and healthy controls (n=11). Patients with FTD were diagnosed according to the Neary criteria (Neary et al. (1998) *Neurology* 51(6):1546-54) and patients with AD were diagnosed according to NINCDS-ADRDA criteria (McKhann et al. (1984) *Neurology* 34:939-944). Disease duration was calculated as the time between the first symptoms reported by the patient or caregiver and the time of clinical examination. Cognitive decline was rated using the Mini-Mental State Examination (MMSE) (Mattis S. "Mental Status Examination for Organic Mental Syndrome in the Elderly Patient". In: Bellak L, Karasu T B, editors. Geriatric Psychiatry. New York: Grune and Stratton, 1976: 77-121). All diagnoses were made by a neurologist. Patients and controls were matched for gender, age, race, marital status and education. FTD subjects ranged in age from 48 to 75 years; AD subjects ranged in age from 50 to 78; and control subjects ranged in age from 49 to 81 years.

All 28 subjects underwent a detailed cognitive assessment prior to any additional evaluation. Detailed medical histories were then taken, and subjects underwent physical and neurological examinations, laboratory screening tests, and neurobehavioural tests.

There was a large standard deviation in MMSE test results in FTD (20±10) and AD (22±8) subjects, but not in control subjects (29±0.33). One FTD subject had a MMSE of 4/30 and one AD subject had a MMSE score of 3/30.

Cognitive Measures

Patients in the study were administered the Behavioural Neurology Assessment (BNA) as part of mental status examination. The BNA was selected for use due to its relative brevity, breadth of coverage of the major cognitive domains, and provision of qualitative as well as quantitative information. The neuropsychological tests shown in Tables 3A and 3B in FIGS. 6A and 6B were used to assess patients initially suspected of suffering from AD and FTD.

Biomarkers

Blood serum samples were taken from each of the subjects. The sera were aliquoted and frozen at −80° C. within two hours of being drawn, and kept frozen until analysis.

Levels of the serum cytokines IL6 and TNF-α, and chemokine IL8, as well as levels of apoptosis mediators Fas-L and caspase-cleaved CK18, were measured by ELISA using commercially available assays according to manufacturers' instructions. TNF-α, IL6, and IL8 levels were measured using a Cytoscreen™ Immunoassay Kit (Biosource International, USA). Fas-L levels (ng/mL) were measured using a Quantikine HS Human sFas Immunoassay (R&D Systems, USA). Caspase-cleaved CK18 levels were measured using a M-30 Apoptosense® ELISA (Peviva AG, Germany). The M-30 ELISA assay utilizes the M5 antibody as a catcher and the M-30 antibody to detect CK18 fragments that contain a neo-epitope (NE) at positions 387-396 generated by the action of caspases 3, 7 and 9 activated during the early stages of apoptosis. The M-30 monoclonal antibody specifically recognizes an epitope at the C-terminus of CK18 which is only exposed following cleavage of CK18 by caspases during apoptosis See the world wide web at (peviva.se/m30-apoptosense-elisa.aspx). Results obtained using the M-30-Apoptosense® ELISA have been shown to correlate with results from other apoptosis assays, including TUNEL and active caspase 3 assays.

The M-30 ELISA uses a series of eight different dilutions of the independent quality control (QC), and the resulting calibration curve for the M-30 ELISA assay has been demonstrated to follow a sigmoid curve with a value of $r^2$ equaling 0.997 and a plateau phase at antigen concentrations starting at 1000 U l$^{-1}$. (see the world wide web at peviva.com).

Protein levels determined by ELISA were quantified using an automatic multi-well microplate spectrophotometer (Maxline Microplate Reader, Molecular Device Corp., USA) in combination with SOFT MAX software 2.3 for Windows.

All measurements were performed in triplicate with a sensitivity and specificity of 95% and 90%, respectively. Measurements were recorded as pg/mL or ng/mL biomarker concentration within a sample.

For IL8, IL6 and TNF-α, the correlation coefficient was linear (r=0.995) at concentrations of 2-500 pg/mL for ILs and TNF-α (r=0.989). For M-30 ELISA, the correlation coefficient was linear (r=0.995) within a concentration range between 50 and 1000 U/mL.

Three plasma aliquots from patients with previously determined low, medium, and high concentrations of analyte were chosen to test between-run precision of the assay. Two normal control plasma samples (quality control—QC) were used to assess between-run imprecision, and were determined from 7 analyte assays with each sample analyzed in duplicate. Between run imprecision was shown to be less than 15%. The within-run precision was determined by calculating the mean values of three samples with low, medium, and high concentrations of analyte following a 20-fold analysis in a single assay. The within-run coefficient of variance (CV) for all analytes ranged from 6.6% to 12%, which was considered to be within the acceptable limit.

Second biomarker level measurements were recorded one year later for 9 control, 3 FTD and 5 AD subjects.

Functional Imaging (ECD and SPECT)

In addition to biomarker level measurement, SPECT imaging analysis was conducted on a subset of subjects. Of the 28 subjects, all controls and 4 of 7 FTD patients received SPECT scan analysis of the brain.

It has been demonstrated that the site of brain lesion is related to specific cognitive deficits. The three data sets were compared in order to assess any relationship between biomarker levels and cognitive impairment and/or lesion location. Associations between biomarker levels and SPECT imaging measures (8 in total) were evaluated by examining the correlation matrix (and the partial correlation matrix) of the 8 SPECT measures with themselves as well as with the cognitive measures (e.g. speech, memory, executive function, attention, concentration, and anxiety).

A Picker 3000, triple-headed gamma camera, and a standardized acquisition and reconstruction protocol were used. Reconstructed images were co-registered to a standardized ECD ($^{99m}$Tc-ethylcysteinate dimer) template derived from 14 healthy elderly subjects. To obtain estimates of regional flow, a region of interest (ROI) template was defined on the MRI from one of these subjects.

Briefly, individual SPECT images were globally transformed to the SPECT template using a 12-parameter, co-registration algorithm. A common transformation for all images into the ROI template space (based on the 6-parameter transform needed to move the standard SPECT image from template space to the standard MRI) was then applied. The data of interest were the mean counts in the ROIs. Given the relatively low spatial resolution of the SPECT images, and the use of average ROI counts across relatively large ROIs (12 cm$^3$ on average), the impact of individual differences in sulcal anatomy were not likely to have a substantial influence on ROI values.

Data Analyses

Associations between biomarker levels and SPECT imaging measures were determined by examining the correlation matrix (and the partial correlation matrix) of the eight measures with themselves—likewise for the cognitive measures. Given that some of the measures were sensitive to common deficits within circumscribed domains, upon confirmation of inter-measure associations, analyses were undertaken using a set of measures reflecting performance in these areas.

Statistical analysis was performed using SPSS 12.0 software for Windows (SPSS Inc., USA). Analysis of Variance (ANOVA) statistical methods were used to evaluate any differences in biomarker levels amongst FTD, AD and control groups.

The relationship between levels of biomarkers and structural and functional neuro-imaging (SPECT) measures was evaluated. Correlation analyses were used to measure potential linear relationships between orbito-frontal atrophy and biomarker levels in an effort to demonstrate correlations with disease severity (as measured by the Mattis Dementia Rating Scale). These analyses were conducted for FTD and control subjects (FIG. 4).

The cognitive measures of FIG. 4, which are correlated with the markers, were derived by a neurologist who reviewed the clinical notes and cognitive test scores available for each patient. The neurologist was blind to biomarker results.

Correlations between cognitive deficit based on neuropsychological examination and biomarkers were made for a subset of AD subjects (FIG. 4.1). In the correlations, it was observed that levels of IL6 were associated with memory impairment and anxiety; levels of IL8 with concentration, attention and executive function impairment; levels of M-30 with executive function and attention impairment; and FAS-L with speech and language impairment in AD subjects.

Results

Figure 3:
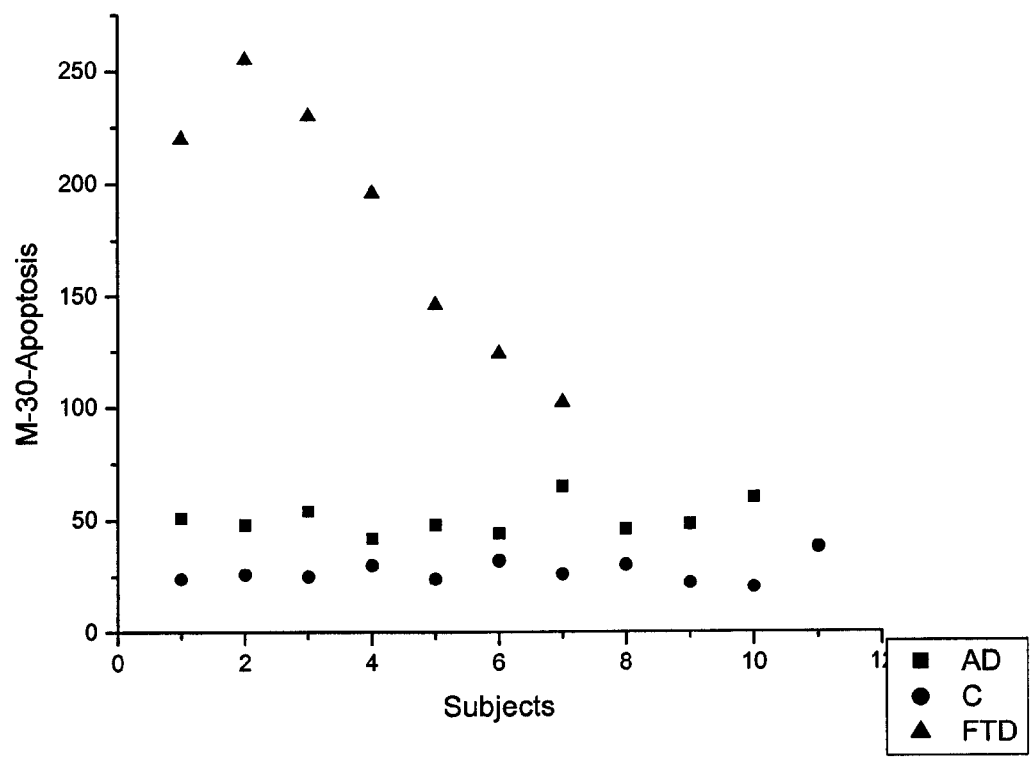
FIG. 3 is a scatter plot of the levels of apoptotic marker caspase-cleaved cytokeratin 18 (CK18) as detected by M-30 antibody in the sera of patients with AD (squares), FTD (triangles), and control patients (circles), further indicating statistically significant ($p<0.001$) decreased levels of caspase-cleaved CK18 in AD compared to FTD. The scatter plot shows the values of apoptotic marker M-30 (U/1000 mL) in sera of the patients with AD (squares) Control (circles) and FTD (triangles). M-30 is statistically lower in AD ($p<0.001$) when compared to FTD.

The levels of IL6 and IL8 were not statistically different between AD subjects, FTD subjects, and control subjects (FIGS. 3.1 and 3.2).

Figure 2:
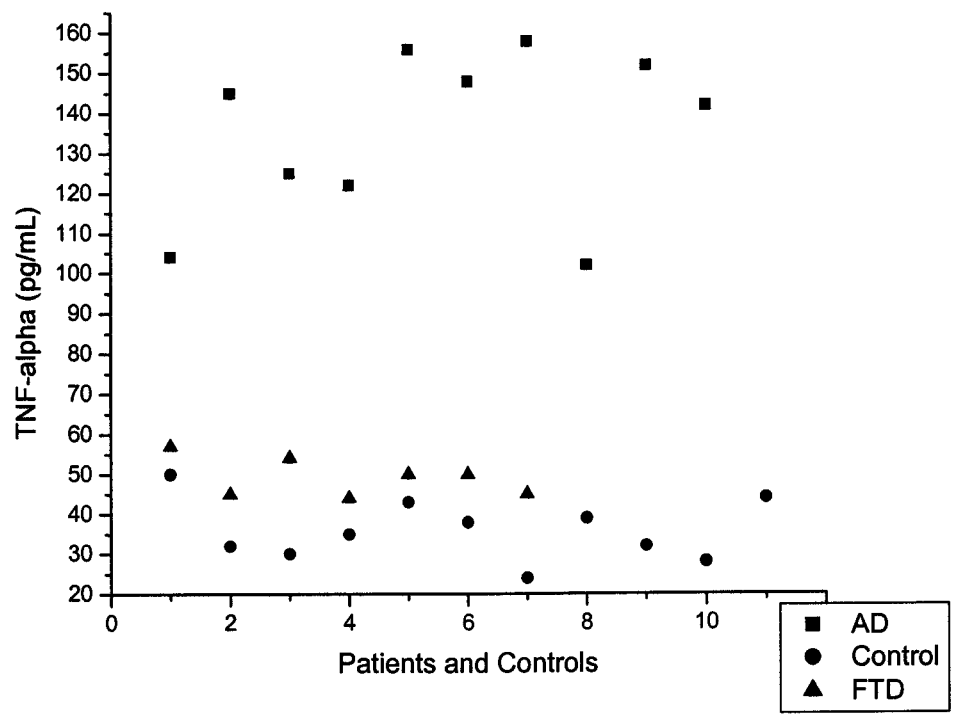
FIG. 2 is a scatter plot of the levels of TNF-α in the sera of patients with AD (squares), FTD (triangles), control patients (circles), further indicating statistically significant ($p<0.001$) elevation of TNF-α levels in AD compared to FTD and controls. The scatter plot shows the values of TNF-α (pg/mL) in sera of the patients with AD (10—squares), Control Patients (11—Circles) and FTD (7—Triangles). TNF-α is statistically higher in AD ($p<0.001$) when compared to FTD and to controls. TNF-α is statistically higher in FTD ($p<0.001$) when compared to controls.

There was a significant difference between levels of TNF-α in control subjects compared to AD subjects, as well as between FTD and AD subjects (p<0.001). There was also a significant difference between levels of TNF-α in control and FTD subjects (FIG. 2).

Significant results were also obtained for FAS-L levels where levels of FAS-L were found to be lower in AD compared to FTD subjects (p<0.001) (FIG. 1). Further, serum levels of Fas-L in control subjects were shown to be lower than those measured in FTD subjects (p<0.001) or AD subjects (p<0.05) (FIG. 1). These data suggest the use of FAS-L serum levels as a marker of AD and FTD but also as a means to distinguish between AD and AD-related FTD.

Similar results were obtained for the M-30 antibody marker of caspase-cleaved CK18 levels (FIG. 3). Significant differences in M-30 antibody-detected caspase-cleaved CK18 levels were observed between FTD and AD subjects (FIG. 3) (p<0.001). There was a significant difference observed for M-30 antibody-detected caspase-cleaved CK18 levels between controls and AD (p<0.05).

One year after initial measurements were taken, subjects were re-evaluated for biomarker levels as well as MMSE. One FTD subject scored lower on MMSE testing (δ 2) and recorded higher levels of apoptosis markers (δ 20 U/1000 mL for caspase-cleaved cytokeratin 18 (CK18) as detected by M-30 and δ 42 ng/mL for sFas-L) compared to previous evaluations. Two of five AD subjects scored lowered on MMSE testing (δ 4 and δ 3) and recorded elevated TNF-α levels compared to previous levels (δ 27 pg/mL and δ 45 pg/mL). These data suggest levels of the disclosed inflammation and apoptosis biomarkers can be used to assess AD and AD-related disorders over time and may be predictive of progression or severity of disease.

In four FTD subjects, SPECT imaging indicated frontal/temporal hypoperfusion, defined as perfusion which is 80% of total cerebellar perfusion. According to the distribution of atrophy and hypoperfusion on neuro-imaging analysis, patients were determined to have predominant frontal involvement. SPECT imaging results were also obtained for two normal control individuals.

From the data, a biomarker level range correlating with disease and stage can be determined (FIG. 7). For example, FAS-L levels in patients with a diagnosis of mild FTD are suggested to be between 70 and 80 ng/mL; for a diagnosis of moderate FTD, levels are estimated to be between 80 and 100 ng/mL; and for a diagnosis of severe FTD, levels are estimated to be over 110 ng/mL. In other words, a sFAS-L measurement of approximately 80 ng/mL, is predictive of FTD. A FAS-L measurement of 40 ng/mL or above is considered abnormal but not FTD.

TNF-α levels above 80 pg/mL can be used to assist diagnosis of AD. Diagnoses of AD severity can be further assisted by determination of TNF-α levels. For instance, diagnosis of "possible", "mild", "moderate", or "severe" may be made for values above 80 pg/mL, 90 pg/mL, 120 pg/mL, and 140 pg/mL, respectively.

In examples 10-13, apoptosis marker caspase-cleaved cytokeratin 18 (CK18) as detected by M-30 levels indicate diagnoses as indicated in the table. In example 14, when Fas-L levels are above the value defined by the 95% upper confidence interval (i.e., mean+2 standard deviations) calculated from a sampling of AD patients, the diagnosis is predicted to be FTD.

Using parameters based on levels of TNF-α, IL6, IL8, FAS-L and M-30 reactivity, degree severity of FTD and AD may be determined. For example, Fas-L levels were shown to correlate with speech and language impairment (FIGS. 4 and 4.1). Therefore, the speech and language components of a patient's cognitive abilities are anticipated to be associated with Fas-L levels. Regarding M-30 reactivity levels, executive function and attention impairment were shown to be correlated with M-30 levels (FIGS. 4 and 4.1).

'Mild', 'moderate', and 'severe' degrees of AD and FTD are indicative of increasing severity of disease. On a graphical scale this might be represented as:

| Less pathological | | ← → | more pathological | |
|---|---|---|---|---|
| 70 | 80 | 90 | 100 | 110 |

In one embodiment, there is provided a method of monitoring the progression of AD and/or FTD by monitoring the levels of these biomarkers over time. As supported by the results, the level in serum of a biomarker collected at a first time (T1) can be compared to its level in serum collected at a second time (T2), in order to determine, quantify, or predict the progression of a disorder. In general, as (level of biomarker at T2–level of biomarker at T1)/(T2–T1) increases, the predicted MMSE will decrease.

In another embodiment, there is provided a diagnostic kit which provides a test score. Test score is calculated from at least one test result that is provided by the kit. If the kit only measures 1 biomarker, then the test score can equal the test result. The test score can be used to provide diagnostic information to the physician. The diagnostic information can be quantitative and/or qualitative. Quantitative information can be provided in the form of assessing the severity of a disorder as mild, moderate, or severe. Qualitative results may include diagnostic categories such as simply "normal/abnormal", AD, AD-like, FTD. Quantitative and qualitative information can be evaluated with respect to a patient's age, sex, medication, stress level, medical history, and other factors, which have been shown to alter biomarker expression. The kit may include manual or computer based implementations of look-up tables such as tables which alter threshold criteria for biomarker levels, based upon a patient's age.

When the kit evaluates a single biomarker, the kit may contain a single antibody and be implemented as 8 rows and 12 columns of wells, which are designed to measure that biomarker. Alternatively, the kit may contain approximately two to six antibodies (wherein the first 2 columns and 8 rows of wells measure the first biomarker and wherein the first column is designed to measure a standard curve and the second to measures the specific biomarker). The standard curve can provide a baseline reference, which is used to evaluate the values derived from the measured biomarker. The reference substance (e.g., a serum known to have a specific level of biomarker) can serve as a quality control for the standard curve. The standard curve can be evaluated with respect to positive as well as negative internal controls. Each kit can contain six channels (biomarkers), with each channel having 8 cells for measuring samples. The role of biomarkers has expanded to become surrogate endpoint in the clinic. However, since biomarker measurements are performed on samples collected from subjects quality assurance and in particular assay validation are essential. Five categories define the majority of biomarker assays from 'absolute quantification' to 'categorical' and the current methods can be realized anywhere within this spectrum. Validation must therefore take account of both the position of the biomarker in the spectrum towards clinical end point and the level of quantification inherent in the methodology.

In one embodiment in which the test is used to derive the progression of the severity of a disorder, the reference substance may be serum that was obtained from the patient at an earlier time (or may include several samples from several earlier time-points). When the test kit evaluates a multiple biomarkers, the kit may contain a several columns of cells each of which are designed to measure each biomarker, and each biomarker may be evaluated according to its own reference substance. Every individual Antibody Bead kit and pre-mixed multiplex kit will come with an information sheet that outlines the performance characteristics for each marker in the assay. In one embodiment, each biomarker will have 95-99% sensitivity (pg/mL); with a specificity, precision of <10% (variance) and a linearity of $R^2$ of about 0.99.

In an additional embodiment, the results of this biomarker testing can be used to prescribe medication. The relative and absolute values of the serum biomarkers disclosed herein can be used to create disease profile for an individual, and medication can be selected based upon this profile. Profiling results from a human serum sample will allow further monitoring of disease progression and treatment efficacy. In addition the results will permit stratification of patients for clinical studies including drug studies. The individual can then be given medications, which have been shown to provide therapeutic benefit for patients with similar profiles.

In an additional embodiment, more than one kit can be used to provide the diagnosis and each kit can contain 1 or more assays such as the ELISA TNF-α assay. The results can be evaluated in terms of statistical probability levels which have been shown to differentiate between the quantifiable concentrations of different biomarkers specific for AD, FTD and controls. The different kits provide results, which are combined during assessment of the patient.

Exemplary Preferred Embodiments

In one example of a preferred embodiment, the instructions will guide a lab technician to operate to achieve approximately the following operations. Blood samples will be collected, as may occur by venipuncture, from the participants and will be placed into EDTA-containing Vacutainer Tubes. The freshly drawn blood will be centrifuged at 3000 g for 20 min at 4° C. Plasma is then separated and subsequently stored at −70° C. in small aliquots. Although fresh samples may be used, normally all analyses will be performed using plasma samples that have been frozen. The aliquots will be defrosted only for 1 series of analysis.

The ELISA-multi Cytokine and Chemokine Kits are the simplest simultaneous multi-analyte enzyme-linked immunosorbent assays (ELISA) Highly specific capture antibodies for key cytokines & chemokines will be placed in a 96-well plate (12 wells×8 wells) that contains 12 strips for testing one or more antigens. The ELISA Kits will be designed to survey a specific panel of cytokines or chemokines involved in AD-inflammation, or FTD-apoptosis serum or plasma.

FIG. 8A shows an example of kit contents and protocols that will be included in the kit. This will enable the collection and analysis of released proteins, for detection of the analytes.

FIG. 8B shows an example of an explanation sheet that can be included in the kit and which relates to operations concerning the sFAS-columns. In addition, the intra-assay and inter-assay coefficients of variance can be provided along with storage and shipping conditions.

FIG. 8C shows an example of directions for running the protocol that would be included in the kit. Note that the within-run precision represents the mean values of 3 samples with low, medium, and high concentrations of the analyte that are analyzed 20 times in 1 assay.

FIG. 9A shows a Kit 1. Kit 1 can be used to detect FTD only and it can also be used to assess measures relating to the severity of the disease. The kit contains 4 analytes. Columns I, II, & III contain assays to measure M 30. Columns IV, V, and VI, contain assays to measure IL 6. Columns VII, VIII, and IX contain assays to measure IL8. Columns X, XI and XII contain assays to measure SFAS. The columns can be used to measure standards (8 duplicates) and samples.

FIG. 9B shows a Kit 2. Kit 2 can be used to distinguish between FTD and AD, and also provides an indication of severity of FTD or AD. Columns I, II, III, and IV contain assays to measure M 30. Columns V, VI, VII, and VIII contain assays to measure TNF-alpha. Columns S IX, X, XI, and XII contain assays to measure sFAS. The kit can contain—8 standards (i.e., 8 standards measured in duplicates) and cells to measure the levels of the analyte in the unknown samples.

FIG. 9C shows a Kit 3. Kit 3 can be used to detect only AD and it can also be used to assess measures relating to the severity of the disease. It will contain 4 analytes. Columns I, II & III contain antibodies to measure the analyte TNF alpha—standards (8 duplicates) and samples Columns IV, V. VI contain assays to measure IL 6. Columns VII, VIII, IX contain assays to measure IL 8. Columns X, XI, XII contain assays to measure sFAS.

In an example of how the kit in FIG. 9C can be used, the first column or "strip" (i.e. coated micro-strips) can contain the quality control standards, where the cells labeled 1 to 8, contain buffer only, 0.625 pg/mL, 6.25 pg/mL, 62.5 pg/mL, 125 pg/mL, 250 pg/mL, 500 pg/mL, 1000 pg/mL. In this series the largest amount of antigen in the quality control substance used to create the standard curve is 1000 pg/mL, the next largest amount is 500 pg/mL. As in the case of the other standards, this can be created by halving the concentration by diluting with twice the amount of buffer, or this standard can be supplied with the kit. In this example, we are halving the concentration used in each proceeding well of the strip in order to get more estimates in the lower concentration range. This increases the accuracy of our estimates for this range. Alternatively, as is well known, the kit may suggest using other values, which may or which may not be ordered in a uniform manner. In other words, instead of dropping from 62.5 pg/mL to one tenth that value (i.e. 6.25 pg/mL) this preceding value could be 31.25 pg/mL, which is 50% rather than 10% of the subsequent value.

In this example the well 9 can contain a blood sample from a first individual being tested, well 10 can contain a second sample from this individual. The two samples may both be serum, plasma, CSF, other fluid, or may be two different types of samples from an individual. Well 11 can contain a low control (e.g., having value in the range of 200 pg/mL) and well 12 can be a high control (e.g., 400 pg/mL). Wells 13 and 14 can contain blood samples from a second individual, while 15 and 16 contain samples from a $3^{rd}$.

In this example, strips 1 (wells 1-8), 4 (wells 25-32), 7 (wells 49-56), and 10 serve to provide quality control curves for assessing the TNF-α, IL6, IL8, and sFas results, respectively. The stop and wash solutions used can be the same for all strips, or alternatively, the wells can be divided into two subgroups, which are separated by a physical barrier which is applied to the plates, and which provides protection when two different liquids are used for the wash. A conjugate, such as HRP conjugate (e.g. 0.4 µL mouse M-30 antibody conjugated to horseradish peroxidase) can also be provided for the different antigens. Additionally, "blocking" may be used by adding a concentrated solution of non-interacting protein, such as Bovine Serum Albumin (BSA) or casein, to at least a portion of the wells. This step is known as blocking, because the serum proteins block non-specific adsorption of other proteins to the plate.

The data supporting the results disclosed herein were obtained using: Cytoscreen™ Biosource Human TNF-alpha immunoassay; Biosource Human IL-6 Immunoassay, Biosource Human IL-8 Immunoassay (Biosource International, Camarillo, Calif., U.S.; supplied in Canada by Medicorp Inc., QC); Quantikine HS Human sFas Immunoassay (R&D Systems; U.S.); and, M-30 Apoptosense™ ELISA (Peviva, Germany). In the kits disclosed herein, the particulars of the kits can be approximately similar to those of these existing kits. This is true with respect to the used: Analytes; Samples; Interfering Substances; Sample Volumes; Sample Stability; Number of Tests (wells) provided; Reagent storage guidelines (e.g. 2-8° C. Do not freeze!); Assay Times: Working Range of the standards; Detection Limits; Reference Range; Reproducibility with respect to Intra-Assay (WA) Precision and Inter-Assay (BA) Precision; Spike Recovery; Linearity/Dilution performance; Hook Effect parameters and limits; Types of Reagents used on Coated Microstrips; Concentrate; Conjugate Dilution Buffers; Standards values (e.g., wells A-G); substances, concentrations and mixtures used for Control Low and Control High; TMB Substrate; Stop Solution; and Wash/Detergent Solutions. This type of information is normally supplied upon an information data sheets supplied with the kits. For example, the sheet may be similar to the M-30 Aptoposense ELISA kits' information sheet for Catalog Prod No 10010 (Peviva, Sweden). However, in the case of the kits currently described the intended use described for the kit can be "The Quantitative measurement of the apoptotic cell death biomarker CK18Asp396-NE ("M-30 antigen") in the assessment of AD and/or FTD. Because apoptosis biomarkers are related to cell-death, the kits may include warning about, and can be contra-indicated for, use for patients having coexisting conditions, which may affect this measurement. For example, a patient who is undergoing chemotherapy, who has recently been in an accident, or who has experience various insults or injuries may display increased apoptosis due to other factors which are unrelated to the pathology associated with particular dementia type. It is expected that the kits would provide similar accuracy to existing kits. Within-day precision using eight replicate independent QCs should be 5-6%. Analyses performed on eight separate days over a 3-month period should yield a between-day precision of 3-10%. Kit-to-kit variations in the concentration of antigen determined in independent QCs should range between 2.5 and 10%.

Enzyme-Linked ImmunoSorbent Assay, or "ELISA", is a biochemical technique used mainly in immunology to detect the presence of an antibody or an antigen in a sample. This test can also be termed an Enzyme ImmunoAssay (EIA) test. The ELISA tests described here can include, or be implemented using, variations on the basic testing techniques, which have been described. The kits can be adopted to use fluorescence or chromogenic ELISA, direct and indirect ELISA methods, competitive ELISA and "sandwich" ELISA methods. As is known, some competitive ELISA kits include enzyme-linked antigen rather than enzyme-linked antibody. The labeled antigen competes for primary antibody binding sites with the sample antigen to be tested (unlabeled). In contrast to the test described in FIG. 9, in this case, the more antigen in the sample, the less labeled antigen is retained in the well and the weaker the signal which is ultimately measured. The detection antibody, which is used can be covalently linked to an enzyme, or can itself be detected by a secondary antibody which is linked to an enzyme, for example, via bioconjugation.

An ELISA may be subject to various types of errors. One type of error is caused by the fact that the biological and chemical reagents used in ELISA can change with time. Another is that the ELISA is not always conducted under appropriate conditions. To rule out such problems, two controls are used. The high control should always produce a positive response if the reagents and conditions are correct. The second control, is the lower control and this should never produce a positive response. It may be included on the information sheet that if either control sample fails to react as expected, then the results for the patient's samples should not be trusted and the assay must be repeated. Additionally, if the ELISA tests are positive (or above a specific threshold level), then the patient can also be retested using other techniques (e.g., western blotting analysis, Terminal uridine deoxynucleotidyl transferase dUTP nick end labeling or 'TUNEL' methods, and other methods of detecting proteins, DNA, RNA segments related to various dementia disorders and symptoms). The current methods are therefore not limited to the use of ELISA tests but also include evaluating these biomarkers using these other types of tests either for primary evaluation of the biomarkers, or for replication or confirmation of result.

The results of the test kits can be evaluated using one or more "cut-off" points between a positive and negative result, and this may be adjusted as a function of age, physical status, or other factor. In addition to clinical implementation on a patient-by-patient basis, the tests kits can be used in clinical research to measure the presence and levels of these analytes and to examine their association with a clinical phenotype as well as the effects of therapeutic interventions. This technology may be particularly useful when sample volume is limited, such as in geriatric studies and clinical trials, especially in order to provide objective metrics of disease state and progression.

The study reported herein characterizes the temporal relationship between serum cytokines and chemokines levels, their expression in poly-morpho-nuclear blood mononuclear cells (PBMC), cerebrovascular abnormalities, and potential functional changes. The data also suggest that pro-inflammatory cytokines in dementia are correlated with age, affective symptoms and intellectual decline to a different degree of the disease. The data also support that the biomarkers can differentiate between FTD and AD.

While the systems and methods have been described in relation to various preferred embodiments, variations can be applied to the technology without departing from the spirit and intent of the invention. Reasonable modification and substitution to the steps of realizing the invention are understood to be covered by this disclosure. The contents of all prior art examples cited in this specification and all scientific/technical references, are hereby incorporated by reference as if recited in full herein. The headers for various sections such as "Background" or "Treatment" are intended to be descriptive only, and do not limit the scope of the material which is provided in these sections, in any way.

The invention claimed is:

1. A diagnostic kit for determining a differential diagnosis in a non-invasive manner in an individual of Alzheimer's disease (AD) versus frontotemporal dementia (FTD) consisting of:
   a) reagents specific for TNF-α, FAS-L, and caspase-cleaved CK18,
   b) instructions for use of the reagents to determine levels of said TNF-α, FAS-L, and caspase-cleaved CK18 in biological samples obtained from such individual,
   c) optionally, a reference substance for each of said TNF-α, FAS-L, and caspase-cleaved CK18 for normalizing data, and
   d) an information sheet for comparing measured levels of said TNF-α, FAS-L, and caspase-cleaved CK18 to reference levels for each of said TNF-α, FAS-L, and caspase-cleaved CK18 to determine whether said individual is suffering from AD or FTD, and/or
   e) an information sheet for comparing the levels of TNF-α, FAS-L and caspase-cleaved CK18 to reference levels for each of said TNF-α, FAS-L and caspase-cleaved CK18 relating to severity of AD or FTD to determine the severity of AD or FTD in said individual.

2. The diagnostic kit of claim 1, wherein said biological samples are peripheral blood samples.

3. The diagnostic kit of claim 1, wherein said information sheets indicate that
   i) a measured level of TNF-α of from about 80 pg/mL to 90 pg/mL is indicative of possible AD;
   ii) a measured level of TNF-α of from about 90 pg/mL to about 120 pg/mL is indicative of mild AD;
   iii) a measured level of TNF-α of from about 120 pg/mL to 140 pg/mL is indicative of moderate AD;
   iv) a measured level of TNF-α greater than 140 pg/mL is indicative of severe AD;
   v) a measured level of FAS-L of from about 70 pg/mL to about 80 pg/mL is indicative of mild FTD;
   vi) a measured level of FAS-L of from about 81 pg/mL to about 105 pg/mL is indicative of moderate FTD;
   vii) a measured level of FAS-L of greater than 105 pg/mL is indicative of severe FTD; and
   viii) a measured level of caspase-cleaved CK18 above 100 U/1000 mL is indicative of FTD.

4. A diagnostic kit for detecting frontotemporal dementia (FTD) in an individual consisting of:
   a) reagents specific for FAS-L and caspase-cleaved CK18,
   b) instructions for use of the reagents to determine levels of said FAS-L and caspase-cleaved CK18 in biological samples obtained from an individual,
   c) optionally, a reference substance for each of said FAS-L and caspase-cleaved CK18 for normalizing data, and
   d) an information sheet for comparing the levels of FAS-L and caspase-cleaved CK18 to reference levels for each of said FAS-L and caspase-cleaved CK18 relating to severity of FTD to determine the severity of FTD in said individual.

5. The diagnostic kit of claim 4, wherein said biological samples are peripheral blood samples.

6. The kit of claim 4, wherein said information sheets indicate that
   i) a measured level of FAS-L of from about 70 pg/mL to about 105 pg/mL is indicative of mild to moderate FTD;
   ii) a measured level of FAS-L greater than 105 pg/mL is indicative of severe FTD; and
   iii) a measured level of caspase-cleaved CK18 above 100 U/1000 mL is indicative of FTD.

\* \* \* \* \*